US008067400B2

(12) United States Patent
Gleicher et al.

(10) Patent No.: US 8,067,400 B2
(45) Date of Patent: Nov. 29, 2011

(54) ANDROGEN TREATMENT IN FEMALES

(75) Inventors: Norbert Gleicher, Chicago, IL (US);
David H. Barad, Closter, NJ (US);
Dwyn V. Harben, Bryn Mawr, PA (US)

(73) Assignee: American Infertility of New York, New York, NY (US)

( * ) Notice: Subject to any disclaimer, the term of this patent is extended or adjusted under 35 U.S.C. 154(b) by 862 days.

(21) Appl. No.: 12/123,877

(22) Filed: May 20, 2008

(65) Prior Publication Data

US 2008/0269180 A1    Oct. 30, 2008

Related U.S. Application Data

(63) Continuation-in-part of application No. 10/973,192, filed on Oct. 26, 2004, now abandoned, and a continuation-in-part of application No. 11/269,310, filed on Nov. 8, 2005, now Pat. No. 7,615,544, and a continuation-in-part of application No. 11/680,973, filed on Mar. 1, 2007, now abandoned.

(51) Int. Cl.
*A61K 31/56* (2006.01)
*A61P 15/08* (2006.01)
*A61K 31/5685* (2006.01)

(52) U.S. Cl. ........................................ 514/170; 514/169
(58) Field of Classification Search ........................ None
See application file for complete search history.

(56) References Cited

U.S. PATENT DOCUMENTS

| 4,670,401 | A  | 6/1987 | Cutler et al. |
|---|---|---|---|
| 4,931,403 | A  | 6/1990 | Cutler et al. |
| 6,221,857 | B1 | 4/2001 | Vandenbergh et al. |
| 6,352,997 | B1 | 3/2002 | Waldstreicher et al. |
| 6,548,087 | B1 | 4/2003 | Kent et al. |
| 2006/0141499 | A1 | 6/2006 | Sher et al. |
| 2007/0155710 | A1 | 7/2007 | Gleicher et al. |
| 2007/0178478 | A1 | 8/2007 | Dhallan et al. |

OTHER PUBLICATIONS

International Searching Authority, PCT International Search Report and Written Opinion, International Application No. PCT/US09/42702, Jun. 22, 2009.
Barbieri RL, et al. Association of body mass index, age, and cigarette smoking with serum testosterone levels in cycling women undergoing in vitro fertilization. Fertil Steril 2005; 83(2):302-8.
Macklou NS, Fauser BC. Aspects of ovarian follicle development throughout life. Horm Res 1999; 52:161-70.

(Continued)

*Primary Examiner* — Johann Richter
*Assistant Examiner* — Erin Hirt
(74) *Attorney, Agent, or Firm* — Beem Patent Law Firm

(57) ABSTRACT

A method of improving cumulative embryo score may comprise administering an androgen to a human female for at least about four consecutive months followed by harvesting and fertilizing oocytes and forming embryos. A method of increasing the quantity of fertilized oocytes in one cycle of in vitro fertilization may comprise administering an androgen to a human female for at least about four consecutive months, harvesting and fertilizing the oocytes. A method of normalizing ovarian DHEA may include administering an androgen for at least about four consecutive months. A method of decreasing the time to pregnancy and increasing the rate of pregnancy by administering an androgen for at least about two months. A method of decreasing miscarriage rates may comprise administering an androgen for at least about two months to a female. Moreover, a method of decreasing aneuploidy rates in human embryos may comprise administering an androgen to a female for at least about two months.

11 Claims, 6 Drawing Sheets

OTHER PUBLICATIONS

Gleicher N, et al. Preliminary evidence that dehydroepiandrosterone (DHEA) increases the chance for the transfer of euploid embryos in women with diminished ovarian reserve.

Gleicher N, Barad DH. The effect of dehydroepiandrosterone on diminished ovarian reserve. Hum Reprod 2006; 21(S-1) i69.

Barad Dh, Gleicher N. The effect of dehydroepiandrosterone (DHEA) on oocyte and embryo yields, embryo grade and cell number in IVF. Hum Reprod 2006;21:2845-9.

Brill H, et al. Dehydroepiandrosterone (DHEA) supplementation and pregnancy outcome: Effect on pregnancy rate and speed of conception. Fertil Steril 2006 (Suppl 1), In press.

Lossi K, et al. Androgen priming using aromatase inhibitor and hCG during early-follicular-phase GnRH antagonist down-regulation in modified antagonist protocols. Hum Reprod Advanced Access, Jun. 19, 2006.

Hsueh AJ, et al. Gonadal cell apoptosis. Recent Prog Horm Res 1996; 51:433-55.

Weghofer A, et al. Aneuploidy rates in embryos from women with prematurely declining ovarian function. Fertil Steril, in revision.

Munne S, et al. Embryo morphology, developmental rates, and maternal age are correlated with chromosome abnormalities Fertil Steril 1995; 64:382-91.

Wu JM, et al. Ovarian aging and menopause: current theories, hypotheses, and research models. Exp Biol Med 2005; 230:818-28.

Munne S, et al. Referring Centers PGD Group. Preimplantation genetic diagnosis significantly reduces pregnancy loss in infertile couples: a multicenter study. Fertil Steril 2005; 85:326-32.

Barad DH, et al. Evidence towards an empiric definition of premature aging ovaries. Fertil Steril (Suppl 1), In press.

Gleicher N, Barad D. Premature ovarian aging and ovarian resistance in young women. Clinical profile and IVF outcome. Fertil Steril, In press.

Taranissi M, et al. Influence of maternal age on the outcome of PGD for aneuploidy screening in patients with recurrent implantation failure. Reprod Biomed Online 2005; 10:628-32.

McNatty KP, et al. The microenvironment of the human antral follicle: interrelationships among the steroid levels in antral fluid, the population of granulose cells, and the status of the oocyte in vivo and in vitro. J Clin Endocrinol Metab 1979; 49:851-60.

Andersen CY. Characteristics of human follicular fluid associated with successful conception after in vitro fertilization. J Clin Endocinol Metab 1993; 77:1227-34.

Hillier SG, et al. Location and developmental regulation of androgen receptor in primate ovary. Hum Reprod 1997; 12:107-11.

Weil S, et al. Androgen and follicle-stimulating hormone interactions in primate ovarian follicle development. J Clin Endocrinol Metab 1999; 84:2951-6.

Gleicher N, et al. Does female androgenization affect the gender offspring.

Grant VJ. Sex predetermination and the ethics of sex selection. Hum Reprod 2006; 21:1659-61.

Hardy ICW. The birds and the wasps: a sex ratio meta-analysis. Trend Ecol Evol 2002; 17:207.

Conover Do, Van Voorhees DA. Evolution of a balanced sex ratio by frequency-dependent selection in a fish. Science, Dec. 1990, vol. 250; 1556-8.

Komdeur J, et al. pre-ovulation control of hatchling sex ratio in the Seychelle warbles. Proc Biol Sci 2002; 269:1967-72.

Veiga JP, et al. Experimentally increased testosterone affects social rank and primary sex ratio in the spotless starling. Horm Behave 2004; 46:47-53.

Krackow S. Potential mechanisms for sex ratio adjustment in mammals and birds. Biol Rev Camb Philos Soc 1995; 70:225-41.

Bouissou MF. Effects of testosterone proprionate on dominance relationships in a group of cows. Horm Behav 1978; 11:388-400.

Udry Jr, et al. Androgen effects on women's gendered behaviour. J Bisoc Sci 1995; 27:359-368.

Grant VJ, France JT. Dominance and testosterone in women. Biol Psychol 2001; 58: 41-47.

Grant VJ, Irwin RJ. Follicular fluid steroid levels and subsequent sex of bovine embryos. J Exp Zool 2005; 303A:1120-5.

Barad DH, Gleicher N. Dehydroepiandrosterone (DHEA) increases pregnancy rates in women with diminished ovarian reserve; a case controlled study. Fertil Steril Submitted for publication.

Azziz R, et al. Androgen excess in women: experience with over 1000 consecutive patients. J Clin Endocrinol Metab 2004; 89:453-62.

Gleicher N. An evolutionary concept of polycystic ovarian disease: does evolution favour reproductive success over survival? Reprod Biomed Online 2006; 12:587-9.

Hofmann, GE et al. High-dose follicule-stimulating hormone (FSH) ovarian stimulation in low-responder patients for in vitro fertilization. Journal of in vitro Fertilization and Embryo Transfer, 1989, 6, 285-289.

Surrey, ES et al. Clinical and endocrine effects of amicrodose GnRH agonist flare regimen administered to poor responders who are undergoing in vitro fertilization. Fertil Steril, 1998, 69, 419-424.

Damario, Ma et al. Dual suppression with oral contraceptives and gonadotrophin releasing-hormone agonists improves in vitro fertilization outcome in high responder patients. Human Reproduction, 1997, 12, 2359-65.

Visser et al. The applicability of the cumulative embryo score system for embryo selection and quality control in an in-vitro fertilization/embryo transfer programme. Human Reproduction, 1993, 8, 1719-1722.

Lutz, et al. Evidence that androgens are the primary steroids produced by Xenopus laevis ovaries and may signal through the classical androgen receptor to promote oocyte maturation. PNAS, 2001, 98, 13728-13733.

Hammes Sr. Steroids and oocyte maturation—a new look at an old story. Molecular Endocrinology, 2004, 18(4), 769-775 (mini review).

Genazzani, et al. Oral dehydroepiandrosterone supplementation modulates spontaneous and growth hormone-releasing hormone-induced growth hormone and insulin-like growth factor-1 secretion in early and late postmenopausal women. Fertility and Sterility, 2001, 76, 241-248.

Morales, et al. Effects of Replacement Dose of Dehydroepiandrosterone in Men and Women of Advancing Age. Journal of Clinical Endocrinology and Metabolism, 1994, 78, 6, 1360-1367.

Muasher SJ. Treatment of low responders. Journal of Assisted Reproduction and Genetics, 1993, 10, 112-114.

Gleicher N, Barad D. Race-based fertility therapy. 2005. Submitted for publication.

Speroff L, et al. Normal and abnormal sexual development. Idem 1999a, pp. 339-379.

Speroff L, et al. Amenorrhea. Idem 1999b, pp. 421-485.

Casson PR, Santoro N, Elkind-Hirsch K, Carson SA, Hornsby PJ, Abraham G, et al. Postmenopausal dehyroepiandrosterone administration increases free insulin-like growth factor-I and decreases high-density lipoprotein: a six-month trial. Fertil Steril 1998;70:107-10.

Gleicher N, Weghofer A, Barad D. Increased euploid embryos after supplementation with dehydroepiandrosterone (DHEA) in women with premature ovarian aging. Fertil Steril 2007;88 (Suppl 1):S232.

Morales C, Sánchez A, Bruguera J, Margarit E, Borrell a, Borobio V, Soler A. Cytogenetic study of spontaneous abortions using semi-direct analysis of chorionic villi samples detects the broadest spectrum of chromosome abnormalities. Am J Med Genet a 1:146:66-70, 2007.

Te Velde ER, Pearson PL. The variability of female reproductive ageing. Hum Reprod Update 2002;8:141-54.

Pal L, Santoro N. Age-related decline in fertility. Endocrinol Metab Clin North Am 2003;32:669-88.

Gleicher N, Weghofer A, Barad D. Preimplantation genetic screening (PGS), "established" and ready for prime time? Fertil Steril; vol. 89, Issue 4, pp. 780-788 (Apr. 2008).

Barad DH, Weghofer A, Gleicher N. Age-specific levels for basal follicle-stimulating hormone assessment of ovarian function. Obstet Gynecol 2007;109:1404-10.

Wright VC, Chang J, Jeng G, Chen M, Macaluso M. Assisted reproduction technology surveillance—United States, 2004; MMWR Surveill Summ 2007;56:1-22.

Levi AJ, Raynault MF, Bergh PA, Drews MR, Miller BT, Scott RT. Jr. Reproductive outcome in patients with diminished ovarian reserve. Fertil Steril 2001;76:666-9.

Golbus MS, Loughman WD, Epstein CJ, Halbasch G, Stephens JD, Hall BD. Prenatal genetic diagnosis in 3000 amniocenteses. N Engl J Med 1997;300:157-63.

Weghofer A, Barad D, Li J, Gleicher N. Aneuploidy rates in embryos from women with prematurely declining ovarian function: a pilot study. Fertil Steril 2007;88:90-4.

Gianaroli L, Magli MC, Ferraretti AP, Munè S. Preimplantation diagnosis for aneuploidies in patients undergoing in vitro fertilization with a poor prognosis: identification of the categories for which it should be proposed. Fertil Steril 1999;72:837-44.

Magli MC, Gianarol L, Ferraretti AP Chromosomal abnormalities in embryos. Mol Cell Endocrinol 2001;183 Suppl 1:S29-34.

Munnè S, Chen S, Colls P, Garrisi J, Zheng X, Cekleniak N, Lenzi M, Hughes P, Fischer J, Garrisi M, Tomkin G, Cohen J. Maternal age, morphology, development and chromosome abnormalities in over 6000 cleavage-stage embryos. Reprod Biomed Online 2007;14:628-34.

Gleicher N, Barad D. "Ovarian age based" stimulation of young women with diminished ovarian reserve results in excellent pregnancy rates with in vitro fertilization. Fertil Steril 2006;86:1621-5.

Kumbak B, Oral E, Kahraman S, Karlikaya G, Garagozoglu H. Young patients with diminished ovarian reserve undergoing assisted reproductive treatments: a preliminary report. Reprod Biomed Online 2005;11:294-9.

Gianaroli L, Magli MC, Ferraretti AP, Tabanelli C, Trombetta C, Boudjema E. The role of preimplantation diagnosis for aneuploidies. Reprod Biomed Online 2002;4 Suppl 3:31-6.

Practice Committees of the Society for Assisted Reproductive Technology and American Society for Reproductive Medicine. Preimplantation genetic testing: a Practice Committee opinion. Fertil Steril 2007;88:1497-1504.

Devroey P, Fauser BCJM. Preimplantation aneuploidy screening: a research tool for now. Lancet 2007;370:1985-6.

Ben-Rafael Z, Fateh M, Flickinger GL, Tureck R, Blasco L, Mastroani L Jr. Incidence of abortion in pregnancies after in vitro fertilization and embryo transfer. Obstet Gynecol 1988;71:297-300.

Ventura SJ, Mosher WD, Curtin SC, Abma JC, Henshaw S. Highlights of trends in pregnancies and pregnancy rates by outcome: estimates for the United States, 1976-96. Natl Vit Stat Rep 1999;15:47:1-9.

Blohm F, Fridèn B, Milsom I. A prospective longitudinal population-based study of clinical miscarriage in an urban Swedish population. BJOG 2008;115:176-82.

Hodges CA, Ilagan A, Jennings D, Keri R, Nilson J, Hunt PA. Experimental evidence that changes in oocyte growth influence meiotic chromosome segregation. Hum Reprod 2002;17:1171-80.

Gleicher, N. et al., Dehydroepiandrosterone (DHEA) reduces miscarriage rates in women with diminished ovarian reserve: a multicenter study, Fertil Steril, vol. 90, Supplement, pp. S258-S259 (Sep. 2008).

Leonidas Mamas and Eudoxia Mamas, "Premature Ovarian Failure and Dehydroepiandrosterone" by published in 2008 by American Society for Reproductive Medicine.

Barad D et al., Update on the use of dehydroepiandrosterone supplementation among women with diminished ovarian function, J Assist Reprod Genet. Dec. 2007; 24(12):629-34. Epub Dec 11, 2007.

Letters to the editor, Augmentation of ovarian response by dehydroepiandrosterone (comments from Peter R. Casson, John E. Buster and Sandra A. Carson), http://humrep.oupjournals.org/cgi/content/full/16/7/1538, Jul. 20, 2004.

Acupuncture May Improve Success Rate of Test-Tube Pregnancies, Acupuncture Today, Jul. 2002, vol. 3, Issue 07.

Gleicher, et al, Update on in Vitro Fertilization approaches, US Obstetrics and Gynecology, vol. 3 Issue 2.

FIG. 1

| DHEA use | Cycle | Date | Cycle FSH mI/Uml | Day 3 Estradiol pg/ml | Peak Estradiol pg/ml | Total Oocytes # | Total Oocytes Mean ± SD[1] | Mature oocyte # | 2pn | Day 3 embryos # | Cryopreserved Mean ± SD[2] |
|---|---|---|---|---|---|---|---|---|---|---|---|
| Early[3] | 1 | 09/03 | 10.59 | 18 | 330 | 1 | 2 ± 1.4 | 1 | 1 | 1 | 2.0 ± 1.4 |
| | 2 | 11/03 | 8.11 | 48 | 619 | 3 | | 3 | 3 | 3 | |
| Mid | 3 | 12/03 | 1.99 | 26 | 975 | 5 | 5.7 ± 1.2 | 5 | 5 | 5 | 5.3 ± 0.6 |
| | 4 | 01/04 | 15.18 | 5 | 908 | 7 | | 7 | 6 | 6 | |
| | 5 | 02/04 | 3.43 | 76 | 901 | 5 | | 5 | 5 | 5 | |
| Late | 6 | 03/04 | 4.96 | 70 | 3251 | 13 | 16.0 ± 3.0 | 12 | 9 | 9 | 10.0 ± 1.0 |
| | 7 | 05/04 | 1.70 | 42 | 3150 | 16 | | 12 | 10 | 10 | |
| | 8 | 06/04 | 2.42 | 75 | 5055 | 19 | | 16 | 13 | 11 | |

[1] (*early* & *mid*) vs. *late*, $p = 0.0001$; *early* vs. *mid*, ns; Linear trend across group $F=51.9$; 1 df; $p = 0.001$
[2] (*early* & *mid*) vs. *late*, $p < 0.001$; *early* vs. *mid*, $p = 0.01$; Linear trend across group $F=82.3$; 1 df; $p < 0.001$
[3] DHEA treatment began 2 weeks before the start of the second cycle on October 6, 2003.

Adrenal function of 17, 20 desmolase (P450c17) *

*Modified from Speroff et al., (1999a); Cytochrome P450 is a generic term used for a group of oxidative enzymes active in steroidogenesis. P450c17 is the enzyme mediating 17-hydroxylas and 17, 20- lyase.

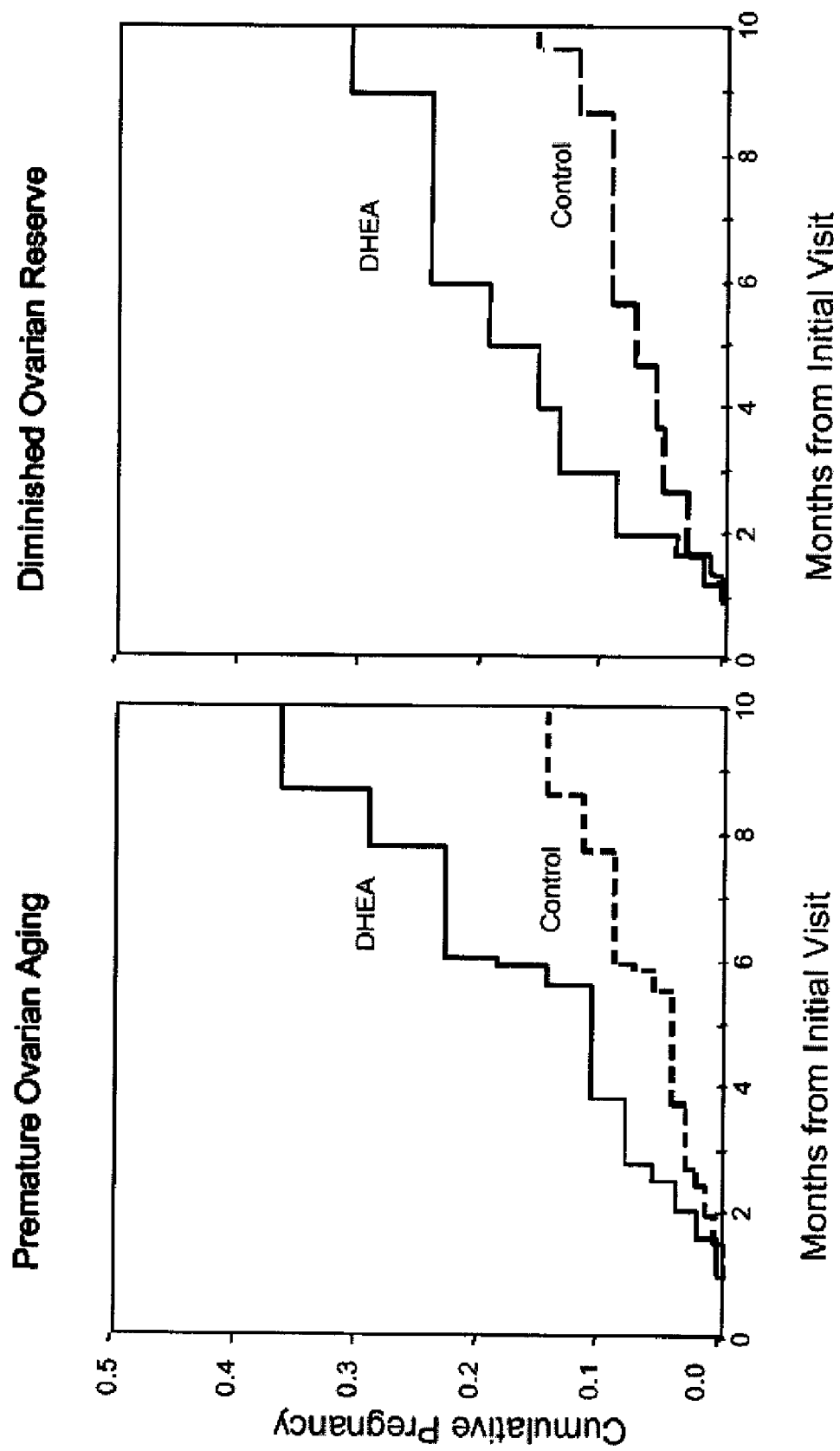

ANDROGEN TREATMENT IN FEMALES

This application is a continuation-in-part of application Ser. No. 10/973,192 filed Oct. 26, 2004 (now abandoned), Ser. No. 11/269,310 filed on Nov. 8, 2005 now U.S. Pat. No. 7,615,544, and Ser. No. 11/680,973 filed on Mar. 1, 2007 now abandoned, which are incorporated by reference in their entirety.

BACKGROUND OF THE INVENTION

1. Field of the Invention

The present invention relates to a method of administering an androgen such as dehydroepiandrosterone (DHEA) for at least two months to a human female, usually one with decreased ovarian function. The administration of DHEA for at least two months has varied and widespread effects such as improving the number and quality of eggs a woman produces along with improving the number and quality of embryos. The administration of DHEA also improves spontaneous pregnancy rates, the in vitro fertilization (IVF) pregnancy rates, cumulative pregnancy rates, and time to conception. Moreover, the administration of DHEA for at least two months reduces miscarriage rates by most likely, at least partially, reducing aneuploidy rates. Further, the administration of DHEA also increases the male to female birth ratio. The method, results, and benefits of DHEA administration for at least two months to a human female are disclosed herein in the description and following examples.

2. Description of the Related Art

The application of assisted reproductive technology has revolutionized the treatment of all forms of infertility. The most common assisted reproductive technology is in vitro fertilization (IVF), in which a woman's eggs are harvested and fertilized with a man's sperm in a laboratory. Embryos grown from the sperm and eggs are then chosen to be transferred into the woman's uterus. Assisted reproductive technology in women depends on ovarian stimulation and concurrent multiple oocyte development, induced by exogenous gonadotropins.

Infertile women are often treated with gonadotropin treatments such as gonadotropin-releasing hormone (GnRH) flare protocols. Estrogen pre-treatment with concomitant growth hormone (GH) treatment is sometimes used in an effort to try and amplify intra-ovarian insulin-like growth factor-I (IGF-I) paracrine effect, which is expressed by granulosa cells and enhances gonadotropin action. However, the clinical utility of combined GH/ovarian stimulation is limited and responses are not dramatic.

Dehydroepiandrosterone (DHEA) is secreted by the adrenal cortex, central nervous system and the ovarian theca cells and is converted in peripheral tissue to more active forms of androgen or estrogen. DHEA secretion during childhood is minimal but it increases at adrenarche and peaks around age 25, the age of maximum fertility, only to reach a nadir after age 60. There is evidence to support use of exogenous DHEA to increase ovulation stimulation in older women who respond poorly to gonadotropin treatments. Older women with diminished ovarian function have decreased egg production and the eggs that are produced usually are of a poor quality. Further, women with diminished ovarian function tend to encounter difficulty becoming pregnant with or without IVF and experience long time periods to conception.

Even when these women do achieve a pregnancy, the rate of a possible miscarriage increases. A large majority of approximately 80 percent of spontaneous pregnancy loss is the consequence of chromosomal abnormalities. As women get older and their ovarian function progressively declines, miscarriage rates rise because of increasing aneuploidy.

Women with diminished ovarian function have largely been considered to be untreatable.

BRIEF SUMMARY OF THE INVENTION

The present invention is directed to the administration of an androgen for at least about four consecutive months to pre-condition ovulation induction in women. In one embodiment, the androgen is DHEA. DHEA administration may be conducted orally in patients. In conjunction with DHEA, high dose gonadotropins may be administered. Also in conjunction with DHEA, follicle stimulating hormone (FSH), norethindrone acetate, leuprolide acetate, and gonadotropin may be used to maximize ovulation induction.

In another aspect of the invention, a method of improving cumulative embryo score may comprise administering an androgen to a human female, for example, DHEA, for at least about four consecutive months followed by harvesting and fertilizing oocytes and forming embryos. Between about 50 mg and about 100 mg of DHEA may be administered to a human female per day. Moreover, a method of increasing the quantity of fertilized oocytes may comprise administering an androgen to a human female for at least about four consecutive months, harvesting and fertilizing the oocytes. Furthermore, a method of increasing the quantity of day 3 embryos from one cycle of in vitro fertilization may comprise administering an androgen for at least about four consecutive months, harvesting and fertilizing the oocytes and forming day 3 embryos.

In a further aspect, the invention relates to methods of normalizing ovarian DHEA levels by administering an androgen to a human female for at least about one month. In a still further aspect, the invention relates to increasing euploid number and rate of oocytes by administering an androgen to a female for at least about four consecutive weeks.

In another aspect of the invention, a method of increasing the male fetus sex ratio may comprise raising androgen levels in a female by, for example, administering DHEA for at least about one month. The fetus and female may both be human and part of an in vitro fertilization process. The androgen level may be raised to above about 250 ng/dl, preferably above about 350 ng/dl. Further, raising androgen levels in an older female to above about 250 ng/dl, preferably above about 350 ng/dl, may decrease the likelihood of a miscarriage.

In yet another aspect of the invention, a method of decreasing miscarriage rates in females may comprise administering an androgen for at least about two months.

In another aspect, a method of decreasing aneuploidy rates in human embryos may comprise administering an androgen to a female for at least about two months.

In a further aspect, a method of decreasing time to pregnancy and increasing pregnancy rates in females may comprise administering an androgen for at least about two months.

BRIEF DESCRIPTION OF THE DRAWINGS

FIG. 1 is a table showing improved ovulation induction with DHEA.

FIG. 6 is a graph showing cumulative pregnancy rate of time from initial visit to clinical pregnancy or censor by DHEA for women with premature ovarian aging.

FIG. 7 is a graph showing cumulative pregnancy rate of time from initial visit to clinical pregnancy or censor by DHEA for women with diminished ovarian reserve.

DETAILED DESCRIPTION OF THE INVENTION

Figure 2:
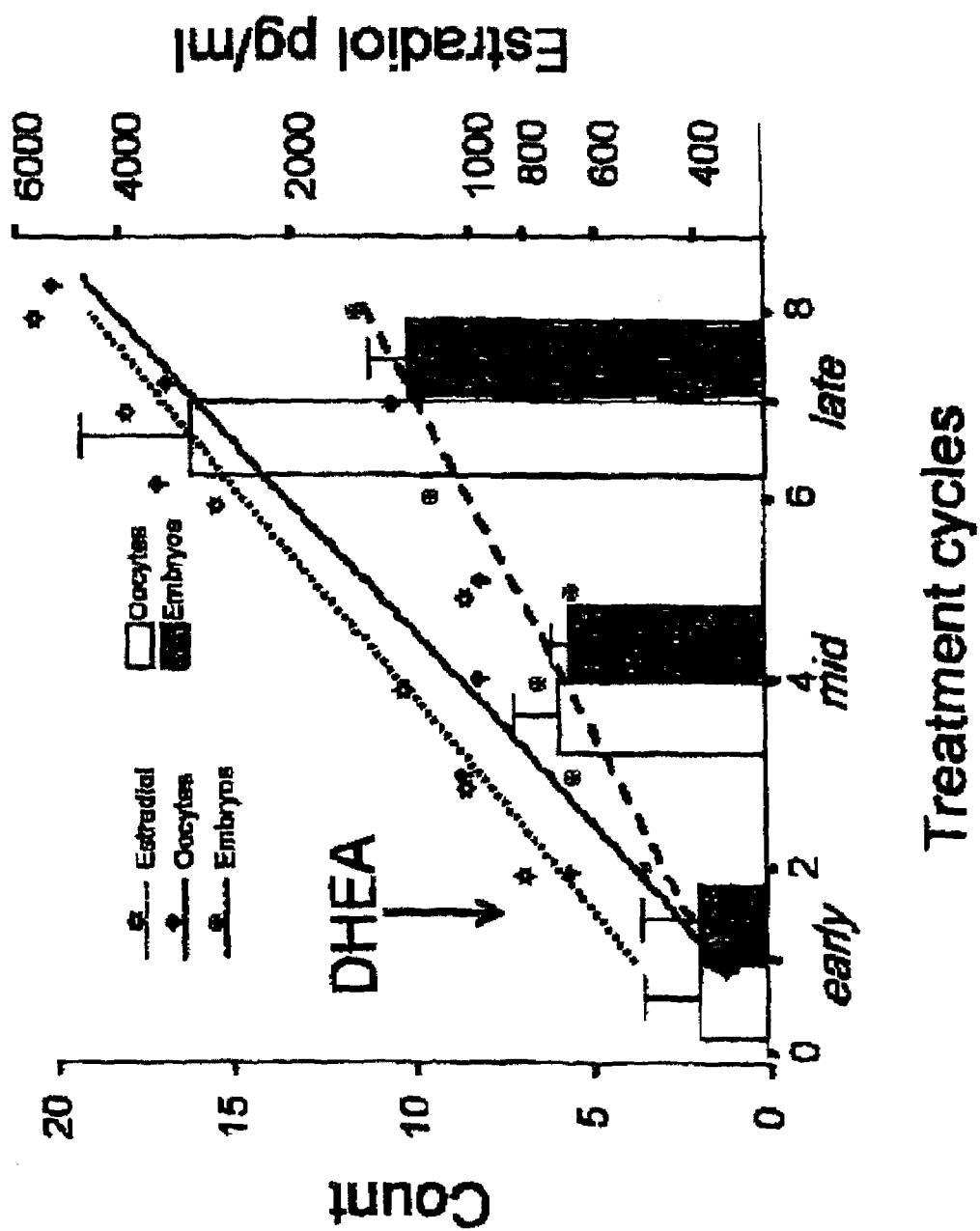
FIG. 2 is a graph showing an increase in the number of fertilized oocytes resulting from oocytes harvested from women with DHEA treatment.

When attempting in vitro fertilization (IVF), older women produce few oocytes and yield few normal embryos, even when exposed to maximal gonadotropin stimulation. The decreased ability of older women to respond to ovulation inducing medications is evidence that ovarian reserve declines with age. Even with IVF cycles, older women produce few oocytes and yield few normal embryos when exposed to maximal gonadotropin stimulation. This change in ovarian responsiveness is known as diminished ovarian reserve or diminished ovarian function.

To improve the number of eggs, the quality of eggs, the number of embryos, the quality of the embryos, spontaneous pregnancy rates, IVF pregnancy rates, cumulative pregnancy rates and time to conception, to reduce the miscarriage rates, and to increase the male/female birth ratio, DHEA is administered for at least two months to a human female in a therapeutically effective amount. Preferably, the human female is a premenopausal human female. The human female may have diminished ovarian reserve. DHEA may be administered to a human female at a dose of between about 50 mg/day and about 100 mg/day, preferably between about 60 mg/day and about 80 mg/day, and in one study about 75 mg/day. Further, DHEA may be administered in a time-release formulation, over the course of the day, or in a single dose. For example, the about 75 mg/day could be administered in a single dose of 75 mg or could be administered as 25 mg three times throughout the day. DHEA is preferably administered orally, although DHEA may be administered or delivered via other methods, such as, but not limited to, intravenously and/or topically. DHEA has a statistically significant effect on the above-mentioned factors after about 2 months of use, but its effect may continue to increase to about four months or about 16 weeks, preferably about four consecutive months or about 16 consecutive weeks, and further may continue past four months of use.

The effects of DHEA increase over time, and may reach peaks after approximately four to five months of supplementation. It is suggested that peaks may occur at four to five months because this time period is similar to the time period of a complete follicular recruitment cycle. Further, the effect of DHEA is suggested to reduce chromosomal abnormalities and thus substantially decreasing miscarriage rates in human females.

I. Improvements in Ovulation

Treatments with an androgen, alone or in conjunction with other hormones, increase a woman's response to ovulation induction, measured in both oocyte and embryo yield. Androgens may be, for example, dehydroepiandrosterone (DHEA) or testosterone. DHEA treatment may be an adjunct to ovulation induction. DHEA taken orally for at least about one month, preferably for about four months, before optionally initiating gonadotropin treatment, may prepare the ovaries for gonadotropin stimulation. A large response may be obtainable by combining gonadotropins and DHEA in treatment for at least about a four month period before an IVF cycle.

Young ovaries are characterized by large numbers of antral follicles and a low rate of atresia. In contrast, older ovaries have few antral follicles, high rates of atresia and exhibit increasing "resistance" to ovulation induction. Older women have decreased oocyte quantity and quality, produce fewer high quality embryos and have lower implantation and pregnancy rates. Most follicular atresia occurs after the primordial follicle resumes growth but before it is gonadotropin responsive enough for recruitment. An induced delay in onset of atresia may salvage follicles for possible ovulation. Interestingly, such an "arrest" of the atretic process has been noted among anovulatory women with polycystic ovary syndrome (PCO). For these women follicles remain steroidogenicaly competent and show evidence of increased aromatase activity compared to like-sized follicles from normal ovaries. Follicular hypersecretion of DHEA, which is typical of PCO, is associated with increased aromatase activity. The increased yield of oocytes and embryos experienced by patients undergoing DHEA treatment may correspond to this underlying physiological process.

II. Improvements to Cumulative Embryo Score

DHEA use beneficially effects oocyte and embryo quality. The observation that DHEA treatment is associated with improved cumulative embryo scores infers that such treatment leads to improved embryo and egg quality. This suggestion is further supported by strong trends towards improved euploidy in embryos and improved pregnancy rates.

DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA has a statistically significant effect on cumulative embryo score after about 2 months of administration, but its effect may continue to increase to about four months, or about 16 weeks, and further may continue past four months of use.

Cumulative embryo score is determined by scoring day 3 embryos and multiplying the number of cells in the embryo by the embryo grade. Embryo grade is a judgment of the embryologist on embryo quality from 1 to 5. Most good embryos are scored 4, with 5 reserved for exceptional embryos. The grade is based on the uniformity of the cells, the color and consistency of the cytoplasm, and the amount of fragmentation. Normal embryos are less than 5% fragmented. A woman with three eight cell embryos each with a grade of four would have a cumulative embryos score of 96, the product of 3×8×4.

A cumulative embryo score for women prior to DHEA use may have been about 34. A cumulative embryo score after DHEA use of at least about four consecutive months may be at least about 90, preferably at least about 95, and in one study at least about 98. The increase in cumulative embryo score may be at least about 56, preferably at least about 60, and in one study about 64. The difference in the cumulative embryo score prior to DHEA use and the cumulative embryo score after DHEA use is statistically significant, p<0.001. The mean increase in embryo score was about 57+/−14.7 after about 16.1 weeks of DHEA administration. As such, DHEA treatment significantly improves the cumulative embryo score.

III. Increase in the Number of Fertilized Oocytes

DHEA treatment significantly increased the number of fertilized oocytes produced by women. DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect on the number of fertilized oocytes after about 4 consecutive weeks. However, DHEA has a significant effect on the number of fertilized oocytes after about 8 weeks or about 2 months of administration, and its effect may continue to increase to about four months, and further may continue past four months of use. Specifically, DHEA treatment has a statistically significant effect after about at least 16 weeks or about at least 4 months of administration.

Figure 3:
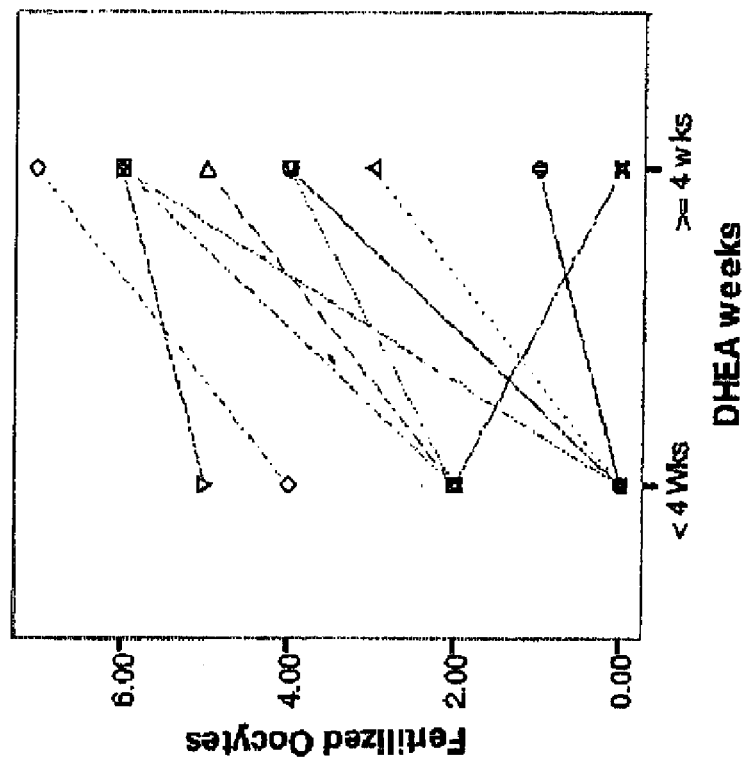
FIG. 3 is a graph showing an increase in the number of fertilized oocytes resulting from oocytes harvested from women with at least 4 weeks of DHEA treatment.

The number of fertilized oocytes produced by women significantly increased after at least about 4 months of consecutive DHEA treatment in 12 women, even though slight improvements were shown after at least about four weeks of consecutive DHEA treatment, as shown in FIG. 3. As shown in FIG. 3, paired comparisons of fertilized oocytes from women having less than about four consecutive weeks of DHEA treatment to the same women having at least about four consecutive weeks of DHEA treatment showed an increase of about 2 fertilized oocytes, or a median increase of about 2.5 fertilized oocytes. The number of fertilized oocytes may show more significant increase after at least about 4 months of DHEA treatment, and may show maximal increase after at least about eight months of DHEA treatment.

IV. Increase in the Number of Day 3 Embryos

DHEA treatment significantly increased the number of day 3 embryos produced by women. DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect of day 3 embryos after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

Figure 4:
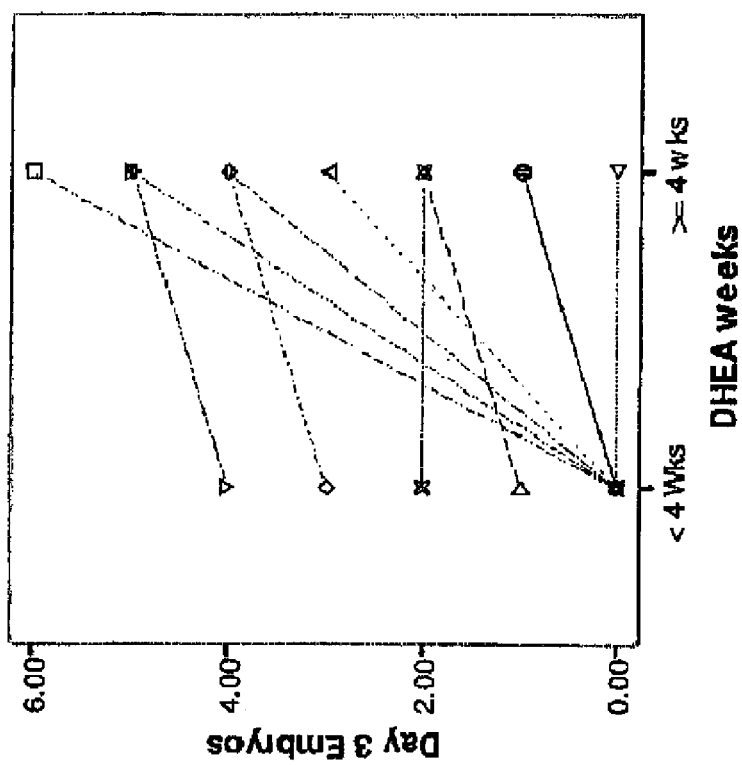
FIG. 4 is a graph showing an increase in the number of day three embryos resulting from oocytes harvested from women with at least 4 weeks of DHEA treatment.

The number of day 3 embryos produced by women also may significantly increase after at least about four months of consecutive DHEA treatment in 12 women, even though slight increases may be shown after at least about 4 weeks of DHEA treatment, as shown in FIG. 4. All of the day 3 embryos included in the study were normal based on their appearance and on the number of cells, i.e. at least four cells. Paired comparisons of fertilized oocytes from women having less than about four consecutive weeks of DHEA treatment to the same women having at least about four consecutive weeks of DHEA treatment may show an increase of about 1 day 3 embryo, and in the study summarized in FIG. 4, an increase of about 2 day 3 embryos. While the number of day 3 embryos produced slightly increased after at least 4 weeks of DHEA treatment, more significant increase occurs after at least about 4 months of DHEA treatment, and maximal increase may occur after at least about eight months of DHEA treatment.

V. Increase in the Number of Euploid Oocytes

DHEA may improve the number of euploid embryos and embryo transfers in women with diminished ovarian reserve (DOR). Pretreatment with DHEA, for at least about one month, preferably at least about four months, in women may increase oocyte and embryo quantity, egg and embryo quality, cumulative pregnancy rates, pregnancy rates with IVF and time to pregnancy.

DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

The prevalence of aneuploidy in embryos, produced through IVF, from 27 consecutive IVF cycles in women with DOR who also had undergone preimplantation genetic diagnosis (PGD) was evaluated. Amongst those cycles, 19 had entered IVF without DHEA treatment and eight had received DHEA supplementation for at least four weeks prior to IVF start.

DHEA treatment may result in higher oocyte numbers (10.4±7.3 vs. 8.5±4.6) increasing from about 8.5 to about 10.4. A significantly larger number of DHEA treated IVF cycles (8/8, 100%) had at least one euploid embryo for transfer than in untreated cycles (10/19, 52.6%; Likelihood ratio, p=0.004; Fisher's Exact Test, p=0.026). Neither absolute numbers of euploid embryos after DHEA nor percentages of euploid embryos differed significantly in this case, however, between untreated and treated patients.

As women age, there is a substantial decline in euploidy rates in embryos produced. Thus, the increase in euploidy results in older women is dramatic evidence of the effectiveness of DHEA in improving embryo quality, and pretreatment with DHEA of women with DOR may significantly increase their chances for the transfer of at least one euploid embryo.

VI. Improvements to Ovarian Function

DHEA may have beneficial effects on ovarian function and oocyte and embryo quality. DHEA substitution may rejuvenate certain aspects of ovarian function in older ovaries. Since DHEA declines with age to a very significant degree, intraovarian DHEA deficiency may be causally related to the ovarian aging process.

Figure 5:
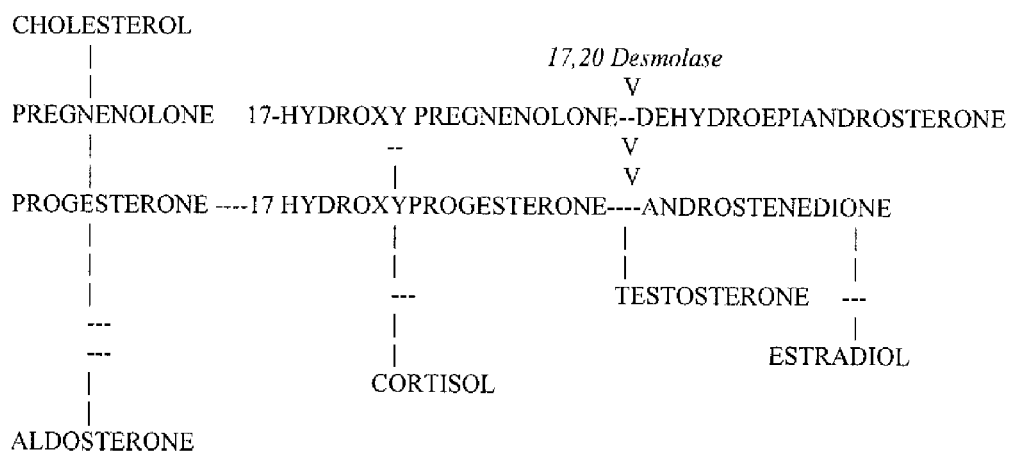
FIG. 5 is a chart showing chemical pathways of adrenal function.

FIG. 5 shows the pathways for normal adrenal function. As shown in FIG. 5, the adrenal enzyme 17,20-desmolase may be responsible for the conversion of 17-hydroxy pregnenolone into DHEA (and the conversion of 17-hydroxyprogesterone into androstenedione) which, based on the two-cell two-gonadotropin theory, may serve in the ovary as a precursor substrate for estradiol and androgens. A patient (Patient B), described further in Example 5 herein, with abnormal 17,20-desmolase (P450c17) function may have a hormone profile characterized by persistently low DHEA, androstenedione, testosterone and estradiol levels, but normal aldosterone and cortisol levels. Patient B exhibited some of the classical signs of prematurely aging ovaries which include ovarian resistance to stimulation, poor egg and embryo quality and prematurely elevated FSH levels.

The decrease in DHEA levels with advancing female age may be an inherent part of the ovarian aging process and may, at least in part, and on a temporary basis, be reversed by external DHEA substitution. This case demonstrates that low DHEA levels are, indeed, associated with all the classical signs of (prematurely) aging ovaries. While association does not necessarily suggest causation, the observed sequence of events in this patient supports the notion that low DHEA levels adversely affect ovarian function.

Patient B was initially thought to have largely unexplained infertility. Approximately 10 percent of the female population is believed to suffer from premature aging ovaries and this diagnosis is often mistaken for unexplained infertility (Nikolaou and Templeton, 2003, Gleicher N, 2005). Patient B later developed signs of prematurely aging ovaries and, finally, showed elevated FSH levels. In the time sequence in which all of these observations were made, Patient B followed the classical parallel premature aging curve (Nikolaou and Templeton, 2003; Gleicher N, 2005).

Once substituted with oral DHEA a reversal of many findings characteristic of the aging ovary was noted. DHEA treatment includes administering a dose of between about 50 mg/day and about 100 mg/day, preferably between about 60 mg/day and about 80 mg/day, and in one study about 75 mg/day to a human female. The DHEA dose could be administered as a single dose or as multiple doses over the course of a day. Particularly, the DHEA treatment may be administered to a premenopausal woman with diminished ovarian function. DHEA may have an effect after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

After DHEA administration, Patient B's DHEA and dehydroepiandrosterone sulfate (DHEAS) levels normalized. In subsequent natural cycles an apparently normal spontaneous follicular response was observed, with normal ovulatory estradiol levels in a patient with persistently low estradiol levels before DHEA treatment.

DHEA deficiency may be a cause of female infertility and may be a possible causative agent in the aging processes of the ovary. The case study involving Patient B also presents further confirmation of the value of DHEA substitution whenever the suspicion exists that ovaries may be lacking of DHEA substrate. Since the process is familial (Nikolaou and Templeton, 2003), it is reasonable to assume that, like other adrenal enzymatic defects, 17,20-desmolase deficiency may occur either in a sporadic or in an inherited form. As both forms will result in abnormally low DHEA levels, both may lead to phenotypical expression as premature ovarian aging.

VII. Increase in Spontaneous Conceptions

Additionally, with DHEA treatment, there may be an unexpectedly large number of spontaneous conceptions in women waiting to go into an IVF cycle. DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect after about 4 consecutive weeks. However, DHEA has a more significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

The DHEA treatment may be at least about 2 weeks before spontaneous conception occurs. In the population of women who are waiting to go into IVF, the spontaneous pregnancy rate is a fraction of about 1% per month. However, in the population of women who have been on DHEA treatment, there were 13 spontaneous pregnancies out of 60 women. As such, DHEA treatment increases spontaneous pregnancies in one study at least about 21 fold. This provides evidence that DHEA works not only in conjunction with gonadotropin stimulation of ovaries, but also without gonadotropin stimulation of ovaries.

VIII. Increase in Male Fetus Sex Ratio

A further effect of DHEA treatment is raising androgen levels in a female to increase the male fetus sex ratio. The gender of offspring may not be solely determined by chance. More highly androgenized female mammals give birth to more male offspring. Androgens, such as DHEA, may be utilized and an elevated baseline level of above about 250 ng/dl, preferably above about 350 ng/dl, may be sufficient. Infertile women with diminished ovarian reserve established a human model to investigate this theory. Data obtained from this model support an effect of androgenization on gender not through a follicular selection mechanism but rather through different mechanisms than previously theorized as evidenced by occurring after the preimplantation embryo stage.

Routine treatment protocol involves administering about 25 mg of micronized, pharmaceutical grade DHEA, TID, to a human female to uniformly raise levels of unconjugated DHEA above 350 ng/dl and, therefore, raise baseline testosterone. In six pregnancies spontaneously conceived, the distribution between female and male offspring was equal, at three and three, respectively. In contrast, in the remaining 15 offspring, which were products of pregnancies achieved through IVF, the distribution was 12 males and 3 females (p=0.035). Amongst women undergoing IVF and PGD, 53 embryos were analyzed from 17 IVF cycles, all having undergone ICSI. The gender distribution was not significantly skewed, with 27 being male and 26 female.

The data, demonstrating a strong trend towards both significance overall and significance (p=0.035) amongst IVF patients, suggest that gender determination may be influenced through hormone environments. The even distribution of gender (27 male and 26 female) in this group of patients argues against a selection process towards male, which is driven by the follicular environment, as has been previously suggested. The even distribution of gender in preimplantation embryos, seen in the control group, also speaks against such an effect.

The only remaining conclusion from the here presented data is that female androgenization affects gender selection after the preimplantation embryo stage and that, by definition, identifies the stage of androgenic influence on gender at or after implantation. All but one IVF cycles in study and control groups underwent ICSI, which requires the removal of granulose cells from the oocyte. One hypothesis is that such a removal may render the local environment more favorable towards the implantation of male than female embryos. A second hypothesis would suggest a similar effect, based on the difference in hormonal milieu in the luteal phase between IVF and spontaneous conception cycles, with the former uniformly supported by progesterone and the latter only sporadically, or not at all. The data provides evidence that the androgenization of females may increase the prevalence of male offspring, especially with IVF.

IX. Increase in Pregnancy Rates

An additional benefit of DHEA treatment is an unexpectedly high number of pregnancies in women, particularly in women with diminished ovarian function. DHEA supplementation is also associated with increased cumulative pregnancy rates and a shorter interval to pregnancy among women with evidence of decreased ovarian function entering evaluation and treatment for infertility.

DHEA treatment includes administering a dose of between about 50 mg/day and about 100 mg/day, preferably between about 60 mg/day and about 80 mg/day, and in one study about 75 mg/day to a human female. Further, DHEA may be administered in a time-release formulation, over the course of the day, or in a single dose. For example, the about 75 mg/day could be administered in a single dose of 75 mg or could be administered as 25 mg three times throughout the day. Particularly, the DHEA treatment may be administered to a premenopausal woman with diminished ovarian function. DHEA may have an effect after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

A case control study of 190 women over 30 years old with diminished ovarian function were studied between 1999 and December 2005. The study group included 89 patients with a mean age of about 41.6 who used supplementation of about 75 mg daily of oral, micronized DHEA for up to four months prior to entry into IVF. The control group composed 101 patients with a mean age of about 40.0 who received infertility treatment but did not use DHEA. The primary outcome was clinical pregnancy after the patient's initial visit.

Ovarian stimulation was identical for study and control groups and consisted of microdose agonist flare, followed by maximal dosage gonadotropin stimulation, using about 300-450 IU of FSH and about 150 IU of HMG. Study patients received DHEA continuously until a positive pregnancy test was obtained or until the patient dropped out of treatment.

Using a developed Cox proportional hazards model, the proportional hazards of pregnancy among women using DHEA was compared with the controls group. The results were that cumulative clinical pregnancy rates were significantly higher in the study group (25 pregnancies of 89 patients for 28% vs. 11 pregnancies of 101 patients for 11%; relative hazard of pregnancy in study group (HR 3.8; 95% CI 1.2 to 11.8; p<0.05)). Specifically, about 28% of the patients that received DHEA achieved a clinical pregnancy, and about 11% of the patients that did not receive DHEA achieved clinical pregnancy. As such, DHEA treatment increases the percentage of clinical pregnancies between about 130% and about 180%, preferably between about 140% and about 170%, and in one study about 157%. As such, DHEA treatment increases clinical pregnancies by at least about 150%.

Further, the results of this study show a statistically significant percentage of women that achieved clinical pregnancy only with DHEA treatment. See Table 8 in Example 7 herein. Table 8 shows 25 of 89 women in the DHEA treated group achieving clinical pregnancy, including 6 of 16 with no other treatment other than DHEA, and 6 of 9 women had intrauterine insemination (IUI/COH) but no IVF. About at least one-half of the patients (or at least about 50% of the patients), a total of 12 out of the 25 women (about 6 of 16 women with no other treatment, and about 6 of 9 women treated with intrauterine insemination) that established pregnancy did so spontaneously (i.e., with no IVF treatment). As such, DHEA treatment also increases the percentage of clinical pregnancies and significantly reduces the cumulative time to pregnancy.

Along with increased clinical pregnancies, women in this study, with a mean age of about 41.6, which were treated with DHEA had decreased miscarriage rates. Specifically, approximately 36% of the women in the control group (4 of 11 women) that did not receive DHEA had miscarriages and, in comparison, only approximately 20% of the women in the DHEA-treated group (5 of 25 women) had miscarriages. As such, DHEA treatment decreased the miscarriage rate between about 30% and about 60%, preferably between about 40% and about 50%, and in one study about 44%. DHEA treatment decreases the miscarriage rate by at least about ⅓, and preferably by at least about ½.

The data, described further herein, provides evidence that the DHEA supplementation improves spontaneous pregnancy rates, IVF pregnancy rates, cumulative pregnancy rates, and decreases the time interval to pregnancy.

X. Decrease in Miscarriage Rates

Supplementation with dehydroepiandrosterone (DHEA) as described herein below decreases miscarriage rates in infertile women with diminished ovarian reserve. DHEA administration, for an average of at least 2 months, decreases the miscarriage rate. DHEA treatment includes administering a dose of between about 50 mg/day and about 100 mg/day, preferably between about 60 mg/day and about 80 mg/day, and in one study about 75 mg/day to a human female. Further, DHEA may be administered in a time-release formulation, over the course of the day, or in a single dose. For example, the about 75 mg/day could be administered in a single dose of 75 mg or could be administered as 25 mg three times throughout the day. Particularly, the DHEA treatment may be administered to a premenopausal woman with diminished ovarian function. DHEA may have an effect after about 4 consecutive weeks. However, DHEA has a more significant effect after about 8 weeks or about 2 months of administration, but its effect may continue to increase to about four months, and further may continue past four months of use. Specifically, DHEA treatment has a statistically significant effect after at least about 16 weeks or at least about 4 months of administration, and preferably, DHEA treatment is administered for at least about 16 consecutive weeks or at least about 4 months.

About 85% of miscarriages are due to chromosomal abnormalities. As such, decreasing the miscarriage rates in women may indicate a decrease in aneuploidy rates.

After about at least two months of prior DHEA supplementation, the rate of clinical miscarriages in 73 pregnancies, established at two independent fertility centers in the United States (U.S.) and Canada, was compared to the national U.S. miscarriage rates, reported for in vitro fertilization (IVF) pregnancies for the year 2004.

The reduction in miscarriage rates in DHEA pregnancies at both centers were similar (15.0% and 15.2%) for a combined reduction in miscarriage rates of about 15.1%. The Mantel-Haenszel common odds ratio (and 95% CI) for the odds of miscarriage with DHEA supplementation, stratified by age, was significantly lower relative to the odds of miscarriage in the general U.S. IVF population [0.49 (0.25-0.94; p=0.04)]. Miscarriage rates after DHEA supplementation was lower at all ages than the 2004 US national averages, but the difference was more pronounced above age 35 years.

More specifically, DHEA treatment decreases the miscarriage rate for women under the age of about 35 between about 5% and about 25%, preferably between about 10% and about 20%, and in one study about 15.7%. DHEA treatment decreases the miscarriage rate for women under the age of about 35 by at least about one-seventh. Further, DHEA treatment decreases the miscarriage rate for women between the ages of about 35 and about 37 between about 50% and about 70%, preferably between about 55% and about 65%, and in one study about 60.8%. DHEA treatment decreases the miscarriage rate for women between the ages of about 35 and about 37 by at least about one-half. Also, DHEA treatment decreases the miscarriage rate for women between the ages of about 38 and about 40 between about 20% and about 40%, preferably between about 25% and about 35%, and in one study about 31.6%. DHEA treatment decreases the miscarriage rate for women between the ages of about 38 and about 40 by at least about ¼, and preferably by at least about ⅓. Additionally, DHEA treatment decreases the miscarriage rate for women between the ages of about 41 and about 42 between about 30% and about 60%, preferably between about 40% and about 50%, and in one study about 45.3%. DHEA treatment decreases the miscarriage rate for women between the ages of about 41 and about 42 by at least about ⅓, and preferably by at least about ½. Further, DHEA treatment decreases the miscarriage rate for women over the age of about 42 between about 40% and about 60%, preferably between about 45% and about 55%, and in one study about 50.1%. DHEA treatment decreases the miscarriage rate for women over the age of about 42 by at least about ½.

DHEA supplementation is associated with a significantly decreased miscarriage rate in women, especially above the age of about 35. DHEA treatment decreases the miscarriage rate for women over the age of about 35 by at least about 30% or at least about ⅓. Supplementation with DHEA reduces the miscarriage risk in this high risk population to levels reported for the general population.

This observation supports a beneficial effect of DHEA on aneuploidy rates. DHEA treated women with diminished ovarian reserve, who produce few embryos, only rarely qualify for preimplantation genetic screening. Data accumulation on embryo aneuploidy rates is, therefore, difficult. Because embryo aneuploidy rates are reflected in miscarriage rates, by demonstrating a remarkable reduction in miscarriage rates, there is circumstantial evidence that DHEA supplementation may reduce the rate of aneuploid embryos in infertile women.

The following examples are to be construed as merely illustrative and not limitative of the disclosure in any way.

EXAMPLE 1

Improved Ovulation

A study including a 43 year old woman, Patient A, undergoing IVF with banking of multiple cryopreserved embryos for future aneuploidy screen and transfer is administered an androgen, namely DHEA. In ten months she undergoes eight treatment stimulation cycles while continuously improving her ovarian response, resulting in oocyte and embryo yields far beyond those previously seen in a woman her age.

Patient A's history is unremarkable except for two previous malarial infections. She is allergic to sulfa medications and has a history of environmental allergies. Her surgical history includes umbilical hernia repair at age one and cholecystectomy at age 21. She had used oral contraceptives for over 10 years. She has no history of irregular menstrual cycles.

Day three serum FSH and estradiol (E2) in her first IVF cycle are 11 mIU/ml and 18 pg/ml, respectively. In subsequent cycles her baseline FSH is as high as 15 mIU/ml. She is given an ovulation induction protocol which is prescribed for patients with evidence of decreased ovarian reserve. Briefly, the protocol includes the following medications: norethindrone acetate tablets (10 mg) for 10 days, starting on day two of menses, followed three days later by a "microdose" dosage of 40 µg of leuprolide acetate, twice daily, and, after another three days, by 600 IU of FSH (Gonal-F; Ares-Serono, Geneva, Switzerland) daily. Peak serum E2 concentration on day nine of stimulation is 330 pg/ml. Following injection of 10,000 IU human chorionic gonadotropin (hCG), she undergoes oocyte retrieval. Only one oocyte is obtained and one embryo is cryopreserved.

Because of the poor response to ovulation stimulation, she is advised to consider donor oocyte or embryo donation. She rejects both options. She starts a second cycle using the same stimulation protocol with one exception: instead of 600 IU of FHS daily, Patient A received 450 IU of FSH and 150 IU of human menopausal gonadotropin (HMG, Pergonal, Ares-Serono, Geneva, Switzerland). This stimulation protocol is continued in identical fashion for the remaining cycles. However, two weeks before starting her second cycle, she begins administration of 75 mg per day of oral micronized DHEA. The date on which she begins administration of 75 mg per day of oral micronized DHEA is Oct. 6, 2003.

Methods of Example 1

The eight treatment cycles are divided into three groups to allow statistical comparison: pre-initiation and very early use of DHEA (early=cycles 1 and 2), initial cycles (mid=cycles 3-5), and later cycles (late=cycles 6-8). Comparison between these categories is by one-way analysis of variance (ANOVA) and multiple comparisons by Student-Neuman-Keuls (SNK) test. The homogeneity of variances and used orthogonal linear contrasts are tested to compare groups and polynomial contrast to test for linear and quadratic trends. All outcomes are presented as mean±1 standard deviation. Rate of change of oocyte counts, cryopreserved embryos and (log transformed) peak estradiol between subsequent cycles is estimated by linear regression.

Embryos are evaluated by the embryologists on day three post-insemination for cell-count and grading. Embryo grading is based on a 1 to 4 scale depending on symmetry, percent fragmentation and appearance of the cytoplasm. All viable embryos are cryopreserved. Statistics are performed using SPSS for Windows, Standard version 10.0.7 (SPSS Co., Chicago, Ill.). Assay of E2 and FSH are performed using the ACS: 180 chemoluminescence system (Bayer Health Care LLC, Tarrytown, N.Y.).

A method of preconditioning ovulation induction in a human female is conceived, comprising administering an androgen in a female for at least about four consecutive months. In one embodiment, the androgen is DHEA. Administration of DHEA for at least about four consecutive months may further comprise administering high dose gonadotropins to the female. Furthermore, DHEA may be administered along with follicle stimulating hormone, human menopausal gonadotropin, norethindrone acetate, leuprolide acetate, and human chorionic gonadotropin. DHEA may be administered orally.

The length of time the androgen is administered to the female can be at least four consecutive months. The DHEA treatment may continue for more than four months. In one embodiment, the androgen administered is DHEA.

Results of Example 1

The results of ovulation induction are displayed in FIG. 1. After eight stimulation cycles and approximately eight months of DHEA treatment, Patient A produced 19 oocytes and 11 cryopreservable embryos. A total of 50 viable embryos have so far been cryopreserved. Significantly more oocytes (p=0.001) and cryopreserved embryos (p<0.001) are obtained in the late cycles (cycles 6-8, 4+ consecutive months of DHEA treatment) compared to the combined early and mid cycles (cycles 1-5, 0-4 consecutive months of DHEA treatment). There is no significant difference in average embryo cell count (6.83±1.37 vs. 7.2±1.15) or morphology (3.6±0.5 vs. 3.7±0.5) between early and mid compared to late cycles. Peak E2, total oocyte, and embryos cryopreserved increase linearly from cycle to cycle, as shown in FIG. 1. Oocyte yield increase 2.5±0.34 oocytes per cycle (p<0.001), cryopreservable embryo yield increase 1.4±0.14 embryos per cycle (p<0.001) and (log) peak E2 increase 0.47±0.06 (p<0.001) across treatment cycles.

The linear increase in (log) peak E2 shown in FIG. 2 represents a cycle to cycle of increase from 123 pg/ml/cycle to 1491 pg/ml/cycle over the eight cycles of treatment. After adjusting for cycle day, the (harmonic) mean E2 is 267 pg/ml (95% confidence intervals (CI) 143 to 498 pg/ml) in the early phase, 941 pg/ml (95% CI 518 to 1712 pg/ml) in the mid phase, and 1780 pg/ml (95% CI 1121 to 2827 pg/ml) in the late phase of treatment. Each of these homogeneous subsets is significantly different from the other (p<0.05) by SNK multiple comparison testing.

The dramatic increase in oocyte and embryo yield experienced by this 43 year old woman is completely surprising and unexpected. Patient A's post-DHEA response to ovulation induction has become more like that of a younger woman with PCO, than that of a 43 year old woman. Since starting DHEA treatment, Patient A has produced 49 embryos of high enough quality to undergo cryopreservation. Sixty percent of those embryos were produced in the last three cycles of treatment, which took place after at least about four consecutive months after starting treatment. After producing only one embryo prior to starting DHEA treatment, Patient A improved by an order of magnitude and produced 13 oocytes and 9 embryos in a cycle after at least about four consecutive months of DHEA treatment, 16 oocytes and 10 embryos in a cycle after at least about five and a half consecutive months of DHEA treatment, and 19 oocytes and 11 embryos in a cycle after at least about seven consecutive months of DHEA treatment.

The increasing numbers of cryopreservable embryos due to DHEA supplementation suggest improved embryo quality.

EXAMPLE 2

Improved Oocyte Fertilization and Cumulative Embryo Score

In another study, thirty (30) patients with evidence of decreased ovarian reserve were given supplemental DHEA 25 mg three times a day, for a total of 75 mg per day, for an average of about 4 months before beginning ovulation induction for IVF. Twelve patients contributed data from cycles both pre-DHEA and post-DHEA, eleven patients contributed data from cycles only pre-DHEA, and seven patients contributed data from cycles only post-DHEA. Patients' response to ovulation induction before DHEA treatment was compared to patients' response to ovulation induction after DHEA treatment with regard to peak estradiol, oocyte production, and embryos transferred and embryo quality.

The thirty patients contributed to data for 42 total cycles, 23 cycles prior to and 19 cycles after starting DHEA supplementation. In comparing the patients as a group pre- and post-DHEA treatment cycles, there were improvements in cancellation rate, peak estradiol, average day 3 embryo cell counts, and embryo grade. However, average oocyte numbers, eggs fertilized, day-three embryos, embryos transferred and cumulative embryo scores increased significantly after DHEA treatment. In logistic regression models adjusted for oocyte number, there was evidence of improved fertilization rates (p<0.005), increased numbers of day-three embryos (p<0.05), and of improved overall embryo score (p<0.01). In 34 IVF cycles that reached the embryo transfer stage, a positive pregnancy test was obtained in zero of 16 cycles with less than an average of about 4 months of DHEA treatment and in 4/18 cycles after an average of 4 months of DHEA treatment.

This case series illustrates that some ovarian function can be salvaged, even in women of advanced reproductive age.

TABLE 1

Univariate comparison of results of in vitro fertililization before and after treatment with DHEA.

|  | Pre DHEA | Post DHEA | p |
|---|---|---|---|
| N | 23 | 19 | |
| Age | 40.9 ± 0.7 | 42.8 ± 0.7 | ns |
| Weeks of DHEA | — | 16.1 ± 2.4 | — |
| Cancellation | 5/21 (21%) | 1/19 (5%) | ns |
| Peak Estradiol | 1018 ± 160 | 1192 ± 904 | ns |
| Oocytes | 3.3 ± 0.7 | 5.8 ± 1.0 | 0.04 |
| Fertilized eggs | 1.3 ± 0.3 | 4.6 ± 0.8 | <0.001 |
| Average Day 3 embryo cell count | 3.1 ± 0.6 | 4.5 ± 0.5 | ns |
| Average Day 3 embryo grade | 2.4 ± 0.3 | 2.8 ± 0.3 | ns |
| Cumulative Embryo Score | 34 ± 6.8 | 98 ± 17.5 | 0.001 |
| Transferred embryos | 1.0 ± 0.2 | 2.6 ± 0.4 | 0.001 |
| Number of Day 3 embryos | 0.9 ± 0.2 | 3.2 ± 0.6 | 0.001 |
| Positive hCG (per transfer cycle) | 0/16 | 4/18 | ns |

Cycle characteristics and responses to treatment are shown in Table 1. The average age of the patients who began DHEA was 41.6±0.6 years. Women in the DHEA group used DHEA for a median value of 16 weeks before their IVF cycle. The cycle cancellation rate was 5 of 21 cycles (21%) pre-DHEA and 1 of 19 (5%) post-DHEA. There was no statistically significant difference in peak estradiol levels between pre- and post-DHEA cycles.

Continuing with the cycle outcomes presented in Table 1, there are improvements in average cell count of day-three embryos and mean embryo grade after DHEA treatment, however the differences are not significant. Mean oocyte numbers, fertilized eggs, day-three embryos, embryos transferred and cumulative embryo scores, all increased significantly after DHEA treatment. In the models adjusted for oocyte number, there was still evidence of increased fertilization rates (1.93 fertilized oocytes, 95% C.I. 0.82-3.04; p<0.005), increased numbers of day-three embryos (1.36 embryos, 95% C.I. 0.34-2.4; p<0.05), and of improved overall embryo score (32.8, 95% C.I. 9.6-56; p<0.01).

FIG. 3 shows paired comparisons of fertilized oocytes (average increase 2.5±0.60; p=0.002) among 12 patients with DHEA treatment cycles of less than about 4 weeks to fertilized oocytes in the same 12 patients after at least about 4 weeks of DHEA treatment. FIG. 4 shows paired comparisons of day 3 embryos (average increase 2.0±0.57; p=0.005) among 12 patients with DHEA treatment cycles of less than about 4 weeks and at least about 4 weeks during IVF cycles. The paired comparisons shows that the mean increase in the number of fertilized oocytes was modest, but significant, (1.42±0.63 increased numbers of fertilized oocytes; p<0.05).

The mean increase in embryo scores was 57±14.7 (p<0.01). The increase in the number of day 3 embryos was 2.0±0.57 (p=0.005) (See FIG. 4) and the increased fertilization quantity was 2.5±0.60 fertilized oocytes per patient (p=0.002) (See FIG. 3). DHEA supplementation improves the average oocyte numbers, eggs fertilized, day three embryos, embryos transferred, and cumulative embryo score.

In addition, DHEA supplementation also improves pregnancy rates and decreases time to pregnancy. Two patients achieved ongoing pregnancies while taking DHEA without IVF; one (43 year old) while using DHEA during a stimulated IUI (intrauterine insemination) cycle and a second (37 year old) conceived spontaneously following an unsuccessful IVF cycle. A third patient (40 year old) also conceived spontaneously while preparing for an IVF cycle; however that pregnancy ended in a spontaneous abortion. In all 7 of 45 (16%) patients using DHEA have conceived and 5 of 45 patients (11%) have experienced continuing pregnancies.

EXAMPLE 3

Increased Euploidy Rate

In another study (data not shown), patients were analyzed after four weeks of DHEA treatment. Seven patients had embryos tested by pre-implantation genetic diagnosis (PGD). In three women who had PGD after less than four weeks of DHEA usage and a mean age 41.5±5.1 at the time of starting IVF cycles, the euploidy, or normal chromosome number, rate was 2/30 embryos (6.6%). In six patients who had PGD after more than four weeks of DHEA usage, and a mean age of 43.7±1.3 years at the time of starting IVF cycles, the euploidy rate increased to (8/27; 29.6%), though this trend did not reach statistical significance. There is a mean age difference between patients who underwent IVF after less than four weeks of DHEA usage (mean age 41.5±5.1) and patients who underwent IVF after at least four weeks of DHEA usage (mean age 43.7±1.3).

As women age, there is a substantial decline in euploidy rates in embryos produced. Thus, the increase in euploidy results in older women is dramatic evidence of the effectiveness of DHEA in improving embryo quality.

EXAMPLE 4

DHEA Treatment Increases Euploidy Number

In a series of studies, it has been documented that DHEA supplementation in women with diminished ovarian reserve (DOR) increases egg and embryo count, improves egg and embryo quality, increases pregnancy rates, and shortens time to conception.

The reports of the studies point towards improvements in follicular recruitment after treatment with androgenic compounds. Since DHEA effects are statistically significant after approximately four months, and since this time period is approximately reflective of the full follicular recruitment cycle, we concluded that DHEA may, at least in part, affect follicular recruitment processes, possibly by influencing apoptosis. Androgens have been reported to affect granulosa cell apoptosis.

While women with prematurely DOR appear to have normal embryonic aneuploidy rates, older women, with physiologic aging ovaries, demonstrate very high aneuploidy rates of their embryos. Increasing aneuploidy rates with advancing female age are, therefore, considered a primary cause for diminishing pregnancy chances, and an increasing miscarriage risk, in older women. Since treatment with androgenic compounds in such patients appears to improve embryo quality and pregnancy chances, it is likely that such treatment positively affects aneuploidy rates.

Materials and Methods of Example 4

All the IVF cycles performed at the Center for Human Reproduction (CHR) in New York, N.Y., between 2004 and 2006 for cycles performed in women with a diagnosis of DOR were retroactively reviewed. The study population, involving 27 IVF cycles, was selected amongst those cycles which, in addition, had undergone preimplantation genetic diagnosis (PGD).

The diagnosis of DOR was made based on previously reported abnormally high, age stratified baseline FSH levels. In practical terms, this meant that a diagnosis of DOR was reached if baseline FSH levels exceeded the 95% confidence interval of age appropriate levels, independent of prior IVF retrievals and/or oocyte numbers. At, or above age 43, all patients were considered to suffer from DOR, independent of baseline FSH level.

Since the year 2004, women with proven DOR, who had undergone at least one prior ovarian stimulation, demonstrating ovarian resistance based on inadequately low oocyte numbers, routinely were offered oral DHEA supplementation (25 mg TID) prior to any further IVF cycle starts. If under age 40, DHEA was given for up to four months prior to IVF. Women of older age received DHEA, if possible, for at least two months.

Women with DOR, who had no proof of ovarian resistance, were not placed on DHEA supplementation until such proof was obtained, unless they were at, or above, age 43 years. IVF cycles on DHEA supplementation have, therefore, to be considered as more severely affected by DOR than those cycles that were conducted without such supplementation. This fact is also reflected by the baseline cycle characteristics of DHEA-treated, and -untreated, patients (Table 2), which demonstrate trends towards older age and higher baseline FSH levels in DHEA treated patients.

TABLE 2

Baseline characteristics of DHEA-treated, and -untreated, patients[1]

| | DHEA-TREATED n = 8 | DHEA-UNTREATED n = 19 |
|---|---|---|
| Age (± SD, year) | 41.2 ± 4.7 | 38.9 ± 5.1 |
| Baseline FSH[2] ± SD (mIU/ml) | 12.4 ± 9.2 | 9.0 ± 2.7 |
| Baseline Estradiol[2] ± SD (pg/ml) | 59.7 ± 32.2 | 68.1 ± 59.1 |

[1]None of the baseline parameters, listed in the table, differed to a statistically significant degree between the two groups.
[2]Reflects highest baseline level of each patient, and not necessarily the baseline level of the IVF cycle.

For the purpose of this analysis, a patient had to be for at least one month (30 days) on DHEA supplementation in order for the IVF cycle to be considered amongst DHEA-treated cycles. All other DOR patients were considered to have received no DHEA treatment. Following this definition, 19 DOR patients had received no DHEA supplementation, and eight had.

All women with DOR, independent of DHEA supplementation, were stimulated with identical protocols, as previously reported in detail elsewhere. In short, they, without exception, received a microdose agonist protocol with maximal goandotropin stimulation of 600 IU to 750 IU daily, with preponderance of FSH, and a smaller daily amount of human menopausal gonadotropin (hMG).

PGD was performed in routine fashion, as also previously described in detail, and involved the analysis of chromosomes X, Y, 13, 16, 18, 21 and 22 by fluorescence in situ hybridization (FISH) on day three after fertilization. Embryo transfer occurred on day five after fertilization.

Patients were represented by only one cycle outcome in each group. If patients had undergone more than one cycle, either with, or without, DHEA supplementation, only their latest cycle was included in the analysis. Three patients underwent both a pre-DHEA and a post-DHEA cycle and in those cases both cycles were included in the analysis.

Statistical analysis was performed using SPSS for windows, standard version 10.0.7. Data are presented as mean±one standard deviation, unless otherwise noted, and statistical differences between the two study groups were tested by Chi-square and (two-sided) Fisher's Exact Test, where applicable, with significance being defined as p<0.05.

Results of Example 4

A total of 27 consecutive IVF cycles in women with DOR who also had undergone preimplantation genetic diagnosis (PGD) were identified and evaluated. Amongst those, 19 had entered IVF without DHEA treatment and 8 had received DHEA supplementation for at least four weeks prior to IVF start.

Table 3 summarizes cycle outcomes.

TABLE 3

IVF cycle and PGD outcomes

|  | DHEA-TREATED | DHEA-UNTREATED |
|---|---|---|
| Peak Estradiol ± SD (pg/ml) | 2310.3 ± 1108.1 | 2123.3 ± 1054.7 |
| Oocytes ± SD | 10.4 ± 7.3 | 8.5 ± 4.6 |
| Embryos ± SD[1] | 9.1 ± 7.3 | 5.7 ± 2.7 |
| n Euploid ± SD | 2.1 ± 1.4 | 1.6 ± 2.3 |
| % Euploid ± SD | 44.1 ± 37.8 | 21.4 ± 27.5 |
| n Aneuploid ± SD | 4.4 ± 3.0 | 3.5 ± 0.3 |
| % Aneuploid ± SD | 55.9 ± 37.8 | 78.6 ± 27.5 |
| Patients with euploid embryos (%) | 8/8 (100)[2] | 7/13 (53.8)[2] |

SD, standard deviation of mean;
[1]Reflects total number of embryos. Since only high quality 6-cell to 8-cell day-3 embryos undergo PGD, the number of embryos tested for ploidy was smaller.
[2]Reflects a statistically significant difference by Likelihood ratio (p = 0.004) and (two-sided) Fisher's Exact Test; p = 0.026. Other comparisons in this table did not reach statistical significance.

DHEA treatment resulted in trends towards higher oocyte numbers (10.4±7.3 vs. 8.5±4.6). A significantly larger number of DHEA treated IVF cycles (eight out of eight, 100%) had at least one euploid embryo for transfer than in untreated cycles (10/19, 52.6%; Likelihood ratio, p=0.004; Fisher's Exact Test, p=0.026). In other words, the primary result reaching statistical significance was the difference in the percentage of IVF cycles which resulted in the transfer of at least one euploid embryo, with DHEA treated patients reaching embryo transfer in 100 percent of cycles, while untreated patients did so in only 52.6 percent of cases.

As can be seen in Table 3, peak estradiol levels, oocyte and embryo numbers and the results of PGD, all demonstrated trends towards a beneficial effect of DHEA. Peak estradiol levels were higher and oocyte, as well as embryo numbers, were larger. There was also a trend towards more euploidy in embryos from treated cycles, both in absolute numbers and in percentages of embryos evaluated by PGD.

Amongst the 27 reported cycles, three patients contributed pre- and post-DHEA cycles. When these cycles were separately analyzed, they demonstrated similar trends as observed for the whole study (Table 4).

TABLE 4

IVF cycle parameters in 3 women with DHEA and - no-DHEA cycles[1]

| Age ± SD (years) | 38.2 ± 5.5 |
|---|---|
| Baseline FSH[2] ± SD (mIU/ml) | 10.5 ± 1.5 |
| Baseline Estradiol[2] ± SD (pg/ml) | 54.4 ± 21.7 |

|  | DHEA-TREATED | DHEA-UNTREATED |
|---|---|---|
| Time pre-/post DHEA (months) | 2.4 ± 2.5 | 1.9 ± 2.2 |
| Oocytes ± SD | 6.0 ± 4.8 | 4.8 ± 1.0 |
| Total Embryos ± SD | 4.0 ± 2.7 | 4.5 ± 0.6 |
| Aneuploid Embryos | 2.0 ± 1.8 | 3.5 ± 0.6 |

SD, standard deviation;
[1]None of the differences between the two study groups reached statistical significance.
[2]Reflects highest baseline level of patients, but not necessarily baseline level during IVF cycle.

Discussion of Example 4

The here presented study demonstrates evidence that DHEA improves, to a statistically significant degree, the number of euploid embryos available for embryo transfer after IVF, and may be at least a partial explanation of why DHEA supplementation improves pregnancy chances in women with DOR. The study also demonstrates a trend towards higher percentages of euploid embryos after DHEA and higher absolute numbers of euploid embryos. The here observed effect of statistically more transferable, euploid embryos, may be due to larger oocyte and embryo numbers, lower aneuploidy rates, or both effects combined.

The mean number of euploid embryos increased after DHEA treatment by approximately one-half embryo. One-half additional embryo, especially if proven euploid, represents significant additional pregnancy potential in women with DOR, who usually produce only relative small embryo numbers. Indeed, this reflects approximately a one-third improvement in euploid embryo yield, and results in the availability of at least one embryo for transfer in all post-DHEA cycles. In comparison, only 52.6% of untreated cycles achieved the same goal. This is a statistically significant difference in embryo transfers. Pretreatment with DHEA of women with DOR significantly increases their chances for the transfer of at least one euploid embryo and may, therefore, at least in part, explain the higher pregnancy rates reported with DHEA supplementation.

Based on the incremental improvement in DHEA effects for up to four months, and the correlation of the time span to a full cycle of follicular recruitment, it is suspect that DHEA may affect apoptotic processes during follicular recruitment. As a consequence, more healthy follicles survive maturation, reach the stage of gonadotropin sensitivity and become subject to exogenous gonadotropin stimulation. These, in turn, also could be expected to have a higher probability of euploidy.

Increasing aneuploidy rates with female age are considered the principle cause of decreasing spontaneous female fertility, increasing infertility and rising miscarriage rates. DHEA may improve euploidy rates as will be discussed in more detail herein, and in turn, improves spontaneous female fertility, decreases the rate of female infertility and reduces miscarriage rates.

EXAMPLE 5

DHEA Substitution Improves Ovarian Function

In a further study, a case of probable 17,20-desmolase deficiency, resulting in abnormally low estradiol, DHEA, androstenedione and testosterone levels, is presented in a woman with a clinical history of, initially, unexplained infertility and, later, prematurely aging ovaries.

This patient started attempting conception in 1996, at age 33. After failing to conceive for over one year, she was diagnosed with hypothyroidism and was placed on levoxyl. She, thereafter, remained euthyroid for the whole period described in this case report. She entered fertility treatment at a prominent medical school based program in Chicago, in August of 1997, where, now age 34, she failed three clomiphene citrate cycles. No further treatment took place until a laparoscopy was performed in October of 1999, at a prominent Atlanta-based infertility center (where the couple had relocated to), revealing stage II endometriosis which was laser vaporized. Following surgery, a fourth clomiphene citrate cycle and a first gonadotropin-stimulated cycle failed. Table 5 presents selected key lab data for all ovarian stimulation cycles the patient underwent. A first in vitro fertilization (IVF) cycle was performed, at age 36, in October of 2000.

This cycle resulted in expected oocyte and embryos yields. Three embryos were transferred, resulting in a chemical pregnancy. Three other embryos were cryopreserved. However, because of a persistently thin endometrium, a number of attempts at transfer were cancelled.

In April of 2001, the patient was, based on an abnormal glucose tolerance test, diagnosed with insulin resistance, and was placed on metformin, 500 mg thrice daily. She had no signs of polycystic ovarian disease: her ovaries did not look polycystic, she was not overweight, had no signs of hirsutism or acne, and androgen, as well as estradiol, levels were in a low normal range (Table 2). In June of 2001 (age 37), a second IVF cycle was initiated. In this cycle the patient demonstrated the first evidence of ovarian resistance to stimulation in that she produced only six oocytes. Only one out of five mature oocyte fertilized, despite the utilization of intracytoplasmic sperm injection (ICSI). The previously cryopreserved embryos were, therefore, thawed and transferred, together with the one fresh embryo from the current cycle. The transfer was unsuccessful.

In August of 2001, the female's FSH level for the first time was abnormally elevated (11.4 mIU/ml), with estradiol levels remaining low-normal. Subsequent FSH levels were 19.1, 9.7 and 9.8 mIU/ml in November and December (twice), respectively, all with low-normal estradiol levels. FSH levels continued to fluctuate in 2002, with levels reported as 11.4 mIU/ml in February, 8.7 in March, 13.6 in June and 19.6 in September, while estradiol levels remained persistently low-normal (Table 2).

A third IVF cycle was started in October of 2002, with a baseline FSH of 11.3 mIUI. Ovarian stimulation, which in the prior two cycles had been given with only recombinant FSH (and antagonists), was now given in a combination of recombinant FSH and hMG at a combined dosage of 300 IU daily. Estradiol levels reached only 890 pg/ml and only 5 oocytes were retrieved. All four mature oocytes fertilized and four embryos were transferred. A twin pregnancy was established by ultrasound and a singleton by heart beat. This pregnancy was, however, miscarried and confirmed as aneuploid with a Trisomy 22.

The fact that this cycle, after the addition of hMG to the stimulation protocol, appeared more successful, led the patient to a search of the medical literature. Like our previously reported patient (Barad and Gleicher, 2005), this patient discovered the case series reported by Casson and associates (Casson et al., 2000). The paper attracted the patient's interest. In follow up, she asked a medical endocrinologist to evaluate her adrenal function. An initial evaluation revealed very low DHEA, DHEA-S, androstenedione and testosterone levels (Table 2). An ACTH-stimulation test was ordered which showed the expected increase in cortisol level, but unchanged, low DHEA, DHEA-S and testosterone levels (Table 3). The patient was advised by her medical endocrinologist that the most likely explanation for such a finding was a 3-beta hydroxysteroid dehydrogenase deficiency. This enzyme defect is, however, associated with an accumulation of DHEA and, therefore, high levels of the hormone. (Speroff et al., 1999a). Such a diagnosis for the patients is, therefore, unlikely. Instead, abnormal 17,20-desmolase (P450c17) function would be expected to result in exactly the kind of hormone profile, reported in this patient after ACTH stimulation, characterized by persistently low DHEA, androstenedione, testosterone and estradiol levels, but normal aldosterone and cortisol levels.

In July of 2003, the patient was started on 25 mg daily of micronized DHEA. After five weeks of treatment, DHEA, DHEA-S and androstenedione levels had normalized into mid-ranges. (Even though androstenedione is partially produced through the activity of 17,20-desmolase from 17-hydroxyprogesterone, part is also derived from DHEA through the activity of 3-beta hydroxysteroid dehydrogenase [Speroff et al., 1999a]. The normalization of androstenedione, after DHEA administration, therefore, also speaks for an underlying 17,20-desmolase defect, and not a 3-beta hydroxysteroid dehydrogenase deficiency.) In the third and fourth month, following the start of DHEA supplementation, the patient ovulated spontaneously with estradiol levels of 268 and 223 pg/ml (Table 2), respectively, measured on the day of LH surge.

On Jan. 28, 2004 (age 39), and after DHEA therapy of approximately six months, a fourth IVF cycle was initiated. Her baseline FSH level in that cycle was 9.6 mIU/ml, estradiol 56 pg/ml. Stimulation took place with 300 IU of recombinant FSH (without hMG) and with an agonist flare protocol. Estradiol levels reached a peak of 1764 pg/ml, 8 oocytes were retrieved, six out of seven mature oocytes fertilized and six embryos were transferred. A triplet pregnancy was established with heart beats. Two, out of the three fetuses lost heart beat spontaneously, and the patient delivered by cesarean section, at term, a healthy singleton male infant.

At surgery, her ovaries were closely inspected and described as "old" and "small", with the left one being described as "almost dead." DHEA and DHEA-S levels at six months of pregnancy were reported at "record lows." DHEA-S, six weeks post-delivery, was still very low (Table 5). At time of this report, the male offspring is nine months old and the mother has been re-started on DHEA in an attempt at another pregnancy.

DHEA substitution resulted in apparently normal peripheral DHEA levels, spontaneous ovulation and normal estradiol production by the ovaries. An IVF cycle, after approximately six months of DHEA substitution, showed, in comparison to a pre-DHEA IVF cycle, improved peak estradiol levels, increased oocyte and embryo numbers and resulted, at age 39, after 6 years of infertility therapy, in a triplet pregnancy and a normal singleton delivery.

Low DHEA levels appear associated with female infertility and ovarian aging. DHEA substitution normalizes peripheral DHEA levels and appears to improve ovarian response parameters to stimulation.

The reported patient exhibited some of the classical signs of prematurely aging ovaries (Nikolaou and Templeton, 2003; Gleicher N, 2004) which include ovarian resistance to stimulation, poor egg and embryo quality and prematurely elevated FSH levels. The patient was initially thought to have largely unexplained infertility. She later developed quite obvious signs of prematurely aging ovaries and, finally, even showed elevated FSH levels.

It has been previously suggested that the decrease in DHEA levels, with advancing female age, may be an inherent part of the ovarian aging process and may, at least in part, and on a temporary basis, be reversed by external DHEA substitution (Barad and Gleicher, 2005, 2005a). This case demonstrates that low DHEA levels are, indeed, associated with all the classical signs of both prematurely and normally aging ovaries. While association does not necessarily suggest causation, the observed sequence of events in this patient supports the notion that low DHEA levels adversely affect ovarian function.

Once the patient was administered oral DHEA, a reversal of many findings characteristic of the aging ovary, were noted. First, the patient's DHEA and DHEA-S levels normalized. In subsequent natural cycles an apparently normal spontaneous follicular response was observed, with normal ovulatory estradiol levels in a patient with persistently low estradiol levels before DHEA treatment (Table 5). The response to ovarian stimulation improved, quantitatively and qualitatively, as the patient improved peak estradiol levels, oocyte and embryo numbers and, as the successful pregnancy may suggest, also embryo quality.

One cannot preclude that other factors contributed. For example, the ovarian stimulation protocol had switched from an antagonist to an agonist flare protocol. The data demonstrates that a maximal effect of DHEA is achieved after at least about four consecutive months of use. This patient was on DHEA treatment for approximately six months before she conceived the pregnancy that led to her first live birth.

This case is well documented in its DHEA deficiency and in its most likely cause. The reported adrenal response to ACTH stimulation (Table 5) lends itself to the explanation (FIG. 1) of 17,20-desmolase deficiency.

TABLE 5

Relevant laboratory results

| Date | TEST | RESULT (Normal values)* | COMMENTS |
|---|---|---|---|
| August 1997 | TSH | 7.8 mIU/l (0.4-5.5) | Diagnosis of hypothyroidism |
| May 1999 | FSH | 4.0 mIU/ml | |
| April 2001 | Glucose tolerance test | Elevated ½ hour insulin levels Normal Glucose levels | Diagnosis of insulin resistance |
| June 2001 | FSH | 7.7 mIU/ml | |
| | Estradiol | 33 pg/ml | |
| August 2001 | Testosterone free/weakly bound | 2 ng/dl (3-29) | Diagnosis of prem. ov. aging |
| | free only | 1 pg/ml (1-21) | |
| | total | 13 ng/dl (15-70) | |
| | DHEA-S | 96 mcg/dl (12-379) | |
| | Total Cortisol | 14.2 mcg/ml (4-22) | |
| | FSH | 11.4 mIU/ml | |
| | Estradiol | 45 pg/ml | |
| October 2001 | Estradiol periovulatory | 119 pg/ml | |
| November 2001 | Testosterone total | 23 ng/ml (14-76) | |
| | Androstenedione | 98 ng/ml (65-270) | |
| | Ovarian antibodies | negative | |
| | FSH | 19.1 mIU/ml | |
| | Estradiol | 23 pg/ml | |
| December 2001 | FSH | 9.7 mIU/ml | |
| | Estradiol | 27 pg/ml | |
| February 2002 | Testosterone total | <20 ng/dl (20-76) | |
| | Androstenedione | 76 ng/dl (65-270) | |
| | FSH | 11.4 mIU/ml | |
| | Estradiol | 28 pg · ml | |
| March 2002 | Testosterone total | 16 ng/dl (15-70) | |
| | FSH | 8.7 mIU/ml | |
| | Estradiol | 29 pg/ml | |
| May 2002 | FSH | 13.6 mIU/ml | |
| | Estradiol | 30 pg/ml | |
| | periovulatory | 139 pg/ml | |
| June 2002 | periovulatory | 50 pg/ml | |
| September 2002 | Testosterone total | 15 ng · dl (15-70) | |
| | free | 1.6 pg/ml (1-8.5) | |
| | % free | 0.0107 (0.5-1.8) | |
| | Estradiol periovulatory | 136 pg/ml | |
| October 2002 | FSH | 11.3 mIUI/ml | |
| | Estradiol | 43 pg/ml | |
| February 2003 | FSH | 13.6 mIU/ml | |
| | Estradiol | 33 pg/ml | |
| March 2003 | FSH | 8.9 mIU/ml | |
| | Estradiol | 67 pg/ml | |
| May 2003 | Anti-adrenal antibodies | negative | |
| | Estradiol periovulatory | 139 pg/ml | |
| | DHEA | 132 ng/dl (130-980) | |
| | DHEA-S | 79 mcg/dl (52-400) | |
| | Testosterone total | 34 ng/dl (20-76) | |
| | free | 3 pg/ml (1-21) | |
| July 2003 | | DHEA TREATMENT START | |
| | DHEA | 296 ng/dl (130-980) | |
| | DHEA-S | 366 mcg/dl (52-400) | |
| | Androstenedione | 121 ng/dl (65-270) | |
| September 2003 | Estradiol periovulatory | 268 pg/ml | |
| October 2003 | FSH | 14.7 mIUI/ml | |
| | Estradiol | 44 pg/ml | |
| | periovulatory | 224 pg/ml | |

TABLE 5-continued

Relevant laboratory results

| Date | TEST | RESULT (Normal values)* | COMMENTS |
|---|---|---|---|
| November 2003 | FSH | 17 mIU/ml | |
| | Estradiol | 38 pg/ml | |
| December 2003 | DHEA | 278 ng/ml (130-980) | |
| | DHEA-S | 270 mcg/dl (52-400) | |
| | Testosterone total | 25 ng/ml (20-76) | |
| | free and weakly bound | 4 ng/dl (3-29) | |
| | free | 2 pg/ml (1-21) | |
| January 2004 | FSH | 18 mIU/ml | $4^{th}$ IVF |
| | FSH | 9.6 mIU/ml | CYCLE START |
| | Estradiol | 56 pg/ml | |
| August 2004 | MID_PREGNANCY DHEA | 74 ng/dl (135-810) | |
| | DHEA-S | 27 mcg/dl (**) | |
| October 2004 | | | DELIVERY |
| December 2004 | DHEA-S | 52 mcg/dl (44-352) | |

*Laboratory tests were performed at varying laboratories
**No pregnancy levels available from laboratory

TABLE 6

ACTH stimulation test

| HORMONE | BASELINE | +30 MINUTES | +60 MINUTES |
|---|---|---|---|
| DHEA-S (mcg/ml) | 87 | 88 | 83 |
| Cortisol total (mcg/dl) | 15 | 26 | 27 |
| Testosterone total (ng/dl) | 28 | 32 | 33 |
| free and weakly bound | 5 | 5 | 5 |
| free | 3 | 3 | 3 |

This case report presents further evidence for DHEA deficiency as a cause of female infertility and as a possible causative agent in the aging processes of the ovary. It also presents further confirmation of the value of DHEA substitution whenever the suspicion exists that ovaries may be lacking of DHEA substrate. Finally, this case report raises the important question what the incidence of adrenal 17,20-desmolase (P450c17) deficiency is in women with prematurely aging ovaries.

EXAMPLE 6

Increase Male Fetus Sex Ratio

Androgenization of females with dehydroepiandrosterone (DHEA), as we recently have been utilizing in the fertility treatment of women with diminished ovarian reserve, in combination with the investigation of spontaneous, versus in vitro fertilization (IVF)-conceived, pregnancies allows for an investigation of the basic theory of sex allocation and its possible pathophysiologic mechanisms.

The treatment protocol for long-term supplementation with DHEA that may improve oocyte and embryo quantity, quality, pregnancy rates and time to conception in women with diminished ovarian reserve, involves 25 mg of micronized, pharmaceutical grade DHEA, TID will usually uniformly raise levels of unconjugated DHEA above about 350 ng/dl, and, therefore, raise baseline testosterone. Estradiol baseline levels may also be raised.

A retroactive review of either ongoing or delivered pregnancies beyond 20 weeks gestational age, conceived while on DHEA treatment for at least 60 days, revealed 23 women. A total of 19 pregnancies were recorded with 16 singleton and 3 twin pregnancies. The medical records of all 19 women were reviewed in order to determine whether they conceived spontaneously, defined as including pregnancies conceived with intrauterine inseminations, or by IVF. If conception had occurred by IVF, it was recorded whether fertilization was spontaneous or by intracytoplasmic sperm injection (ICSI).

As a control group, seven women were selected who had undergone one IVF cycle with preimplantation genetic diagnosis (PGD), while for at least 60 days on DHEA supplementation, but had not conceived. The PGD data, defining each embryo's gender, were recorded. Statistics were performed using a binomial runs test, comparing seen distributions with an expected distribution of 50 percent, with $p \leq 0.05$ defining significance.

Sixteen singleton pregnancies resulted in 11 males and 5 females (N.S.). Two of three twin pregnancies were heterozygous and one homozygous. If outcomes of both heterozygous twins, but of only one homozygous twin, were added, the final gender distribution was 15 males and 6 females (p=0.078, N.S.)

Amongst six pregnancies, spontaneously conceived, the distribution between female and male offspring was equal, at three and three, respectively. Whereas amongst the remaining 15 offspring, which were products of pregnancies achieved through IVF, the distribution was 12 males and 3 females (p=0.035). Only one IVF patient failed to have ICSI. Amongst women undergoing IVF and PGD, 53 embryos were analyzed from 17 IVF cycles, all having undergone ICSI. The gender distribution was not significantly skewed, with 27 being male and 26 female.

This study allows for the dissection of the conception process into its various stages and, therefore, permits an analysis of, not only the basic question whether androgenization does indeed, affect gender selection in the human, but also how such a selection may be influenced.

The here presented data, demonstrating a strong trend towards significance overall, and significance (p=0.035) amongst IVF patients, suggest, convincingly that gender determination may be influenced by hormonal environment. Assuming an effect of androgens on gender selection, such women should give birth to a preponderance of male offspring. Confirming such a finding could present a potential additional explanation for the evolutionary preservation of PCOS in practically all human races.

EXAMPLE 7

Increase Pregnancy Rates

In an additional study, a retrospective analysis of a 190 women with diminished ovarian function above 30 years old, who were treated between 1999 and December 2005 was completed to assess the impact of DHEA supplementation on the time interval to the establishment of pregnancy.

A prequalification for each patient's diagnosis of diminished ovarian function was either a sub-diagnosis of premature ovarian aging (POA) or a sub-diagnosis of diminished ovarian reserve (DOR). POA was, in turn, defined as baseline follicle stimulating hormone (b-FSH), on Day 2/3 of a cycle as <12 mIU/ml, but exceeding the 95% CT of the mean value for the patient's age group.

Specifically, this meant b-FSH≧7.4 mIU/ml at age 30-34 years and ≧8.6 mIU/ml at age≧35 years. DOR, in turn, was defined as b-FSH≧12 mIU/ml and/or a baseline estradiol level≧75 pg/ml. 49 patients were confirmed with POA and 52 patients were confirmed with DOR, creating a control group of 101 women. Because of potential impending loss of ovarian function in the control group women, the control group women were treated with IVF as soon as possible.

During the time studied, the study group consisted of 89 patients, with diminished ovarian function (POA 24, DOR 65). Each person in the study group was placed on DHEA supplementation. The DHEA supplementation included administering about 25 mg of (pharmaceutical grade) micronized DHEA, three times daily, for up to about four months (mean 3.8±0.3 months). In contrast to the control group, women in the study group did not enter IVF right away. This delay of IVF treatment allowed the possibility of spontaneously conceived pregnancies. Those patients who did not conceive spontaneously within four months of beginning DHEA entered IVF.

Methods of Example 7

Ovarian stimulation was identical for study and control groups and comprised microdose agonist flare, followed by maximal dosage gonadotropin stimulation, using about 300-450 IU of FSH and about 150 IU of HMG. Study patients received DHEA continuously until a positive pregnancy test was obtained or until the patient dropped out of treatment. DHEA and DHEAS levels were monitored monthly, and patients were interviewed at each visit about adverse reactions to DHEA supplementation. Because of the dynamics of the DHEA treatment algorithm, at the time of this data analysis, 16 women in the study group were at various stages of DHEA supplementation, prior to any intervention, 9 women received ovarian stimulation while on DHEA, and 64 have undergone an IVF cycle.

In order to assess the impact of DHEA supplementation on time interval to the establishment of pregnancy, this study was designed as a life-table analysis, measuring not only total pregnancy rates but also the time between initial presentation and end of last treatment intervention.

Each recorded clinical pregnancy, defined as positive fetal cardiac activity on ultrasound examination after 6 weeks, was recorded as a positive outcome. Patients who continued treatments beyond the study period or stopped treatments were considered right censored data at the end of the study period, or at treatment cessation, respectively.

The following factors were compared between study and control groups: female age, months of infertility prior to initial visit, length of treatment from first presentation, gravidity, race, IVF treatments, maximal baseline FSH levels, maximal baseline estradiol levels, IVF cycle cancellation rates, oocyte numbers, number of embryos transferred, implantation rates, cumulative clinical pregnancy rates and miscarriage rates.

A Cox regression analysis was used to evaluate time-to-event. The model that we used stratified for level of ovarian reserve (POA and DOR) and adjusted for age, day 3 FSH, fertility treatments (none, Intrauterine Insemination and controlled ovarian hyperstimulation (IUI/COH), or IVF) and race/ethnicity. A trend in pregnancy rates over months of DHEA exposure with an interaction term for time and DHEA months of exposure was tested. SPSS for Windows, Standard version 10.0.7 (SPSS Co. Chicago, Ill.) was utilized for data analysis. Continuous outcomes are presented as mean±1 standard error. Univariate comparisons were made with analysis of variance, or by using Fisher's exact test.

Results of Example 7

Table 7 summarizes patient characteristics. As can be seen, study patients were slightly older than the controls at 41.6±0.4 and 40.0±0.4 years (p<0.05) respectively. Pregnancy histories, duration of infertility and of treatment (in months) were similar between the two groups. Controls represented a non significant larger proportion of minorities, received more treatment cycles overall (1.6±0.9 versus 1.3±1.0; p<0.05) and differed significantly in the various treatments they received (p<0.001). Study patients demonstrated a non-significantly higher b-FSH 16.0±1.2 13.6±1.0 mIU/ml) and a significantly higher baseline estradiol level (366±53 versus 188±24 pml/ml; p<0.05). More women in the study group had b-FSH≧10 mIU/ml that amongst controls (73% versus 51.5%; p<0.05). In addition, greater proportion of women in the study group had DOR (p<0.005).

TABLE 7

Characteristics of DHEA Treated and Controls

| | DHEA | Control | p |
|---|---|---|---|
| N | 89 | 101 | |
| Age | 41.8 ± 0.4 | 40.0 ± 0.4 | <0.05 |
| Months Infertility | 44.5 ± 4.8 | 41.9 ± 5.9 | ns |
| Months from First Visit | 8.1 ± 0.7 | 7.8 ± 1.0 | ns |
| Race | | | ns |
| White | 82 (70.5%) | 57 (56.4%) | — |
| Hispanic | 7 (7.9%) | 12 (11.9%) | — |
| Black | 9 (10.2%) | 14 (13.9%) | — |
| Asian | 11 (12.5%) | 18 (17.8%) | — |
| Cycles of Treatment | 1.3 ± 1 | 1.6 ± 0.9 | <0.05 |
| Treatment | | | <0.01 |
| No Treatment | 16 (18.2%) | 0 (0%) | — |
| IUI/COH | 9 (10.2%) | 0 (0%) | — |
| IVF | 64 (71.6%) | 101 (100%) | — |
| Day 3 FSH (mIU/ml) | 16.0 ± 1.2 | 13.6 ± 1.0 | ns |
| Day 3 E2 (pmol/ml) | 366 ± 53 | 198 ± 24 | <0.05 |
| Ovarian Function | | | <0.005 |
| POA | 24 (27%) | 49 (43.5%) | — |
| DOR | 65 (73%) | 52 (51.5%) | — |

Table 8 lists the results of univariate comparisons of treatment outcomes. As can be seen, confirming a more severe degree of diminished ovarian function, the study group produced significantly fewer oocytes, normal day-3 embryos (2.4±0.03 versus 3.5±0.2; p<0.05) and transferred embryos (2.1±0.2 versus 2.7±0.2; p<0.05). Cycle cancellations were, however, nominally higher among the controls (25.7% versus 14.3%).

TABLE 8

Univariate Comparison of Results Between Control and DHEA Treated Patients

| | DHEA | Control | p |
|---|---|---|---|
| N total; (IVF) | 69; (64) | 101 | |
| Months of DHEA | 3.8 ± 0.3 | — | — |
| Cancellation (IVF) | 9/63 (14.3%) | 26/101 (25.7%) | ns |
| Oocytes | 3.9 ± 0.4 | 5.8 ± 0.5 | <0.01 |

TABLE 8-continued

Univariate Comparison of Results Between
Control and DHEA Treated Patients

|  | DHEA | Control | p |
|---|---|---|---|
| Normal Day 3 embryos | 2.4 ± 0.3 | 3.5 ± 0.2 | <0.05 |
| Transferred embryos | 2.1 ± 0.2 | 2.7 ± 0.2 | <0.05 |
| Positive hCG (>25 mIU/ml) | 26/86 (30%) | 18/101 (18%) | ns |
| Implantation (FH/Embryos trans) | 13/101 (11.4%) | 11/148 (6.9%) | ns |
| Clinical Pregnancy | 25/69 (28.1%) | 11/101 (10.9%) | <0.01 |
| No Treatment | 6/16 (35.3%) | — | — |
| IUI/COH | 6/9 (66.7%) | — | — |
| IVF | 13/64 (20.6%) | 11/101 (11.9%) | ns |
| Miscarriage (Per clinical Pregnancy) | 5/25 (20%) | 4/11 (36%) | ns |

Overall clinical pregnancy rates were significantly higher in study patients (28.1% versus 10.9%; p<0.01). Remarkably, almost one-half of all pregnancies in the study group were established spontaneously before IVF start; however, even within the patients reaching IVF, there was a strong trend towards higher pregnancy rates (20.6% versus 11.9%).

Approximately two months after initiation of treatment the mean DHEA and DHEAS levels at cycle day 2 blood drawing were in the low normal ranges. Few patients reported side effects from DHEA use. These included mild transient acne on the face, chest or back, oily skin and mild hair loss. No facial or body hair growth was reported, nor was there any deepening of voice. Some patients reported an increased sense of well-being or increased libido.

Cox regression of months from initial visit until clinical pregnancy, adjusted for age, race/ethnicity, fertility treatment, and stratified for level of ovarian reserve (POA and DOR), revealed that DHEA treated patients had a significantly increased proportional hazards ratio for clinical pregnancy relative to controls (HR 3.8; 95% CI 1.2 to 11.8; p<0.05). FIGS. 6 and 7 show proportional hazard curves of clinical pregnancy by months from their initial visit. Specifically, FIG. 6 is a graph showing cumulative pregnancy rate of time from initial visit to clinical pregnancy or censor by DHEA for women with premature ovarian aging, and FIG. 7 is a graph showing cumulative pregnancy rate of time from initial visit to clinical pregnancy or censor by DHEA for women with diminished ovarian reserve. The curves reveal a rapidly separating increase in cumulative clinical pregnancies between study and control groups from the first month on.

Extended Cox models with correction for time dependent variables "months of DHEA use" and "Treatment" did not decrease the proportional hazards estimation of pregnancy associated with DHEA treatment (HR 4.8; 95% CI 1.6 to 14.2; p=0.005).

Discussion of Example 7

A significantly increased pregnancy rate in a group of women with a very poor prognosis for pregnancy has been determined. A strength of this study is its rather large sample size.

Spontaneous background pregnancy rates in average infertile women occur at an approximate rate of one to two percent per month. Spontaneous pregnancies in women with clear evidence of diminished ovarian function are obviously an even rarer occurrence. Given the degree of loss of ovarian reserve in this group, a 28.1% cumulative pregnancy rate in a patient population, previously largely referred into oocyte donation, is quite remarkable.

DHEA supplementation can improve ovarian function in women with diminished ovarian reserve. Study and control patients received identical ovarian stimulation protocols during IVF cycles. IVF protocols during the study years 1999-2005 did not significantly change during this time. Specifically, the protocols may include administering microdose agonist/gonadotropin stimulations in women with diminished ovarian reserve.

The mechanism of DHEA's action on the ovary remains speculative. DHEA declines with age and DHEA supplementation may simply improve the substrate pool for steroidogenesis, since DHEA is a precursor hormone for estradiol and testosterone.

Androgens may, however, influence ovarian follicular growth not only by acting as metabolic precursors for steroid production, but also by serving as ligands for androgen receptors or by other, non-classical mechanisms. During ovulation induction with exogenous gonadotropins, DHEA is the prehormone for up to 48% of follicular fluid testosterone, which is, in turn, the prehormone for estradiol. There is evidence that androgens act, together with FSH, to stimulate follicular differentiation. Androgens are also known to promote steroidogenesis and follicular recruitment and to increase insulin-like growth factor (IGF-1) in the primate ovary. DHEA-treated rat ovaries express elevated levels of IGF-1 in pre-antral and early antral follicles.

A transient increase in IGF-1 in patients undergoing exogenous gonadotropin ovulation induction after pretreatment for only eight weeks of DHEA has previously been reported and it was hypothesized that the effect of DHEA on ovulation induction might have been mediated by increased IGF-1.

Higher baseline testosterone levels have been associated with improved IVF outcomes, and higher serum testosterone has been correlated with higher oocyte numbers retrieved at IVF. Some authors have suggested that improved outcomes in women with diminished ovarian reserve after co-treatment with aromatase inhibitors may be the consequence of induction of FSH receptors on granulosa cell by androgens. The resultant ovarian response may then lead to improved follicular survival, increased follicle numbers and higher estradiol levels during stimulation, as classically also observed in polycystic ovarian disease.

Human polycystic ovaries have been described as representing a "stock-piling" of primary follicles, secondary to an alteration at the transition from primordial to primary follicle. It is possible that DHEA treatment may create PCO like characteristics in the aging ovary. Long term exogenous androgen exposure can induce PCO-like histological and sonographic changes. Androgens have been reported to suppress apoptosis. Exogenous DHEA exposure may occur during the first two weeks of pregnancy.

In summary, a significant increase in the odds of pregnancy among DHEA treated women has been determined. This increase appears to be rapid in onset and to continue progressively within eight months of initial observation.

EXAMPLE 8

Decrease Miscarriage Rates

In a further study, women (i.e, women with progressively declining ovarian function) with diminished ovarian reserve were administered DHEA to assess the effect of DHEA on miscarriage rates.

Since women with diminished ovarian reserve produce only few oocytes and embryos, preimplantation genetic diagnosis (PGD) in association with IVF is only rarely indicated, and, indeed, may be detrimental. To accumulate direct ploidy data on a large enough statistical patient sample is, therefore, difficult. Because spontaneous miscarriage rates are reflective of aneuploidy rates, the study presented herein includes pregnancy outcomes after DHEA supplementation from two independent North American fertility centers and compares those with age-specific national outcome data after IVF.

Materials and Methods of Example 8

Based on reported clinical experiences, the indications for DHEA supplementation have changed over the years, with women above age 40 since 2007 receiving routine supplementation, and younger women receiving supplementation only selectively. This means that under age 40 women receive supplementation only if they demonstrate elevated age-specific baseline follicle stimulating hormone (FSH) levels and have demonstrated in at least one cycle inappropriately low oocyte yield with in vitro fertilization (IVF) following standard ovarian stimulation with gonadotropins.

DHEA supplementation involves the use of pharmaceutical grade micronized DHEA at a dosage of about 25 mg, three times daily. Patients are on DHEA supplementation for at least about two months prior to oocyte retrieval. This period of minimal pretreatment is based on the recognition that at two months pregnancy curves between DHEA pretreated and control patients statistically diverge. DHEA is maintained until pregnancy is established and is discontinued with positive pregnancy test.

Toronto West Fertility Associates, in Toronto, Canada, started utilizing DHEA independent of the use of DHEA at the Center for Human Reproduction (CHR) in New York, N.Y. In December of 2007, Toronto's medical director forwarded a detailed electronic record of the center's all-inclusive DHEA experience for analysis to CHR. This study, therefore, reports on the miscarriage rate of pregnancies, independently established under DHEA supplementation at both fertility centers, and compares these rates, age-stratified, to miscarriage rates reported in a national IVF data base in the U.S. for the year 2004. The definitions of clinical pregnancy, and of miscarriage, used herein follow the reporting requirements of this national data base, defining a clinical pregnancy as a pregnancy, confirmed by ultrasound examination.

It is important to note that DHEA supplemented patients universally suffered from severely diminished ovarian reserve. Their pregnancy expectations were, therefore limited. Patients who conceived a clinical pregnancy, thus, represented only a minority of DHEA supplemented patients at both centers.

Miscarriage rates of DHEA supplemented patients were compared with national IVF outcome statistics, reported annually under Federal mandate by the Centers for Disease Control. The data utilized for this study reflect 2004 United States national statistics. Pregnancy and miscarriage rates at the two centers were pooled after confirmation of homogeneity of variance. Common odds ratios of the pooled miscarriage rates among age stratified pregnant patients were compared between the pooled rates and the 2004 US national rates utilizing the Mantel-Haenszel common odds ratio. Statistical analyses were performed using SPSS Windows, standard version 15.0.

Results of Example 8

New York reported 40 and Toronto 33 DHEA pregnancies, for a combined DHEA pregnancy experience of 73 pregnancies. New York reported six miscarriages, for a clinical miscarriage rate of 15.0%, and Toronto reported five miscarriages, for a clinical miscarriage rate of 15.2%, for a combined miscarriage rate of 11/73 (15.1%). For analysis, the 2004 miscarriage rate in the national U.S. registry of 17.6% was used.

Figure 8:
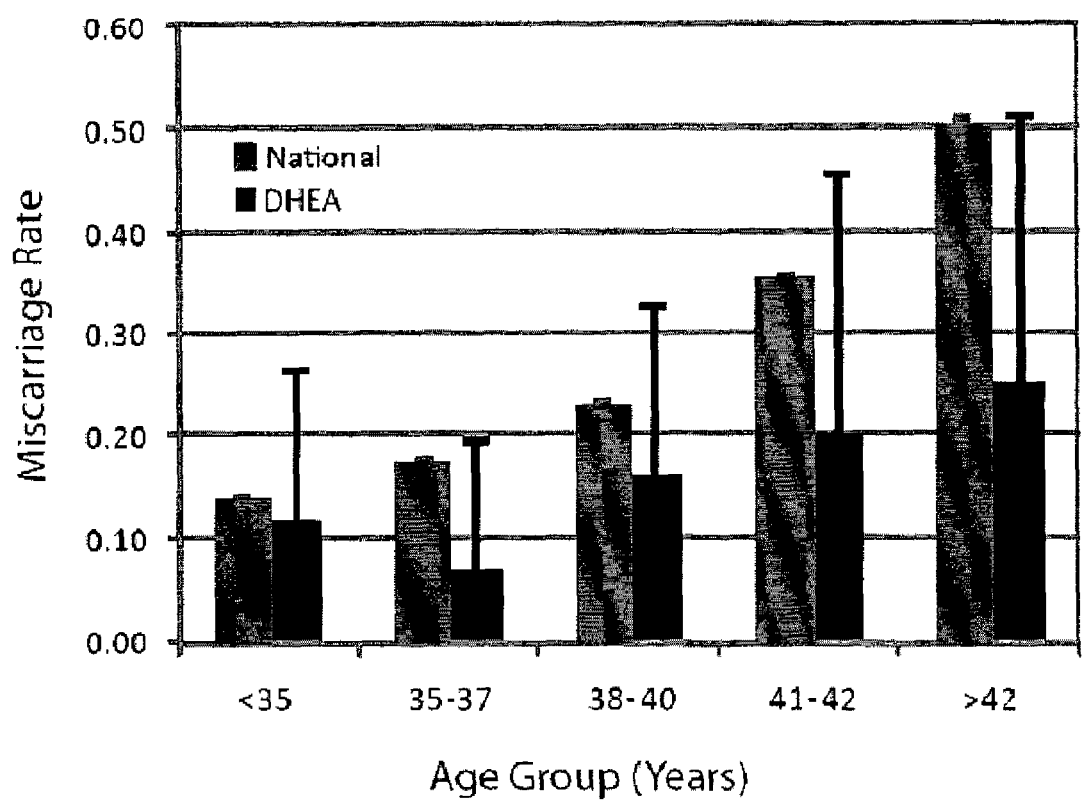
FIG. 8 is a graph showing a comparison of miscarriage rates between DHEA treated infertility patients and 2004 national US IVF data.

As seen in Table 9 (below) and FIG. 8, miscarriage rates after DHEA supplementation, stratified for age, were lower at all ages [OR 0.49 (0.25-0.94; p=0.04)]. The decrease in miscarriage rate was, however, especially apparent above age 35 years.

TABLE 9

Age-stratified pregnancy and miscarriage rates

| | Age (years) | | | | |
|---|---|---|---|---|---|
| | <35 | 35-37 | 38-40 | 41-42 | >42 |
| DHEA Pregnancies | | | | | |
| NY | 10 | 5 | 6 | 10 | 9 |
| TO | 7 | 10 | 13 | 0 | 3 |
| Miscarriages | | | | | |
| NY | 1 | 0 | 0 | 2 | 3 |
| TO | 1 | 1 | 3 | 0 | 0 |
| Misc. Rate (%) | | | | | |
| NY | 10.0 | 0.0 | 0.0 | 20.0 | 33.3 |
| TO | 14.3 | 10.0 | 23.1 | — | 0.0 |
| TOTAL | 11.8 | 6.7 | 15.8 | 20.0 | 25.0 |
| (±95% CI) | (15.0) | (13.0) | (16.0) | (25.0) | (25.0) |
| NATIONAL | | | | | |
| Misc. Rate (%) | 14.0 | 17.1 | 23.1 | 36.6 | 50.1 |
| (±95% CI) | (1.0) | (1.0) | (1.0) | (2.0) | (5.0) |
| Decrease in Misc. Rate with DHEA (%) | −15.7 | −60.8 | −31.6 | −45.3 | −50.1 |

Miscarriage rates after DHEA supplementation, stratified for age, were lower at all ages [OR 0.49 (0.25-0.94; p = 0.04)]. The decrease in miscarriage rate was, however, especially apparent above age 35 years.
NY, - Center for Human Reproduction, New York;
TO, - Toronto West Fertility Associates, Toronto, Canada Discussion of Example 8

The data reported herein demonstrate a significantly diminished miscarriage rate in women with diminished ovarian reserve, in comparison to a standard IVF population, if pretreated for at least two months with DHEA. Specifically, as shown in Table 9, the percentage decrease in miscarriage rate with DHEA supplementation for women with diminished ovarian reserve under the age of 35 was 15.7, for women between the ages of 35-37 was 60.8, for women between the ages of 38-40 was 31.6, for women between 41-42 was 45.3, and for women above the age of 42 was 501. This effect appears particularly pronounced above age 35 years.

This is a remarkable observation that is further strengthened by the fact that, due to their severely diminished ovarian reserve, the studied DHEA supplemented women represent a highly unfavorable patient population. It has been reported that women with diminished ovarian reserve experience exceedingly high miscarriage rates, far in excess of standard IVF patients with normal ovarian reserve. For example, miscarriage rates of 57.1 percent under age 35 in women with diminished ovarian reserve, 63.5 percent between ages 35 and 40 in women with diminished ovarian reserve, and as high as 90 percent above age 40 years in women with diminished ovarian reserve have been reported. Considering the fact that national U.S. IVF data represents only a minority of women with diminished ovarian reserve, the finding that DHEA supplementation significantly reduced miscarriage rates in all age groups below those of an average national IVF population is remarkable.

While on first glance the larger degree of reduction in miscarriage rate in older women may surprise, it should not. Aneuploidy rates increase with age and, indeed, age 35 is generally considered the age cut off, where more aggressive prenatal genetic screening becomes indicated. If DHEA affects aneuploidy rates, then one would, indeed, expect a much larger beneficial effect after, rather than before, age 35, because older women usually produce fewer embryos, and the relative benefit from a decrease in aneuploidy rate on the number of euploid embryos transferred in IVF will, therefore, increase with advancing female age.

Aneuploidy is a frequent finding even in young women. As women age, the prevalence of aneuploidy increases further, at times reaching close to 90 percent in women above age 40. Interestingly, women who demonstrate clinical evidence of prematurely aging ovaries do not also demonstrate prematurely enhanced aneuploidy rates. They maintain the expected age-specific aneuploidy, dictated by their chronological age, and therefore, experience similar implantation— and pregnancy rates, though, because of decreased oocyte and embryo numbers, reduced cumulative pregnancy rates. It, therefore, should not surprise that women under age 35, even though suffering from a significant degree of prematurely diminished ovarian reserve, did not benefit as much from DHEA as older women.

This study demonstrates a statistical association between DHEA supplementation and decreased miscarriage rates. The reported data offers enough circumstantial evidence to suggest that DHEA both decreases miscarriage rates and reduces aneuploidy rates in human embryos.

The presented data helps to explain why DHEA supplementation increases egg and embryo quality, improves pregnancy rates and speeds up time to conception. Egg and embryo quality is, of course, at least partially a reflection of ploidy. Embryos with less aneuploidy can be expected to lead to more pregnancies, resulting in more, and quicker, conceptions.

The concept of embryo selection by improving ploidy has been the basis for attempts at improving pregnancy rates and reducing miscarriage rates via preimplantation genetic screening (PGS). The utility of PGS has recently, however, been seriously questioned since, especially in women with only few embryos, the necessary embryo biopsy may cause more harm to pregnancy chances than the potential benefits, derived from embryo selection offer. DHEA supplementation, therefore, may represent a much simpler, more cost effective and, most importantly, safer method of embryo selection for ploidy than PGS.

It should not be overlooked that the here presented study addresses only infertile women with a significant degree of diminished ovarian reserve. As already noted, they represent a very unfavorable patient population, with exceedingly high expected miscarriage rates. However, even though infertile women with normal ovarian reserve have significantly lower miscarriage rates, they in general still experience higher miscarriage rates than the average population. While the here-reported miscarriage rates in DHEA patients are remarkably low, caution should, therefore, be exercised in concluding automatically that the observed DHEA effect can be extrapolated to a general population. It is, however, quite remarkable that the here-reported miscarriage rates in women with severely diminished ovarian reserve at both study centers, stratified by age, were practically identical to those reported for the general population.

Based on the hypothesis that congression failure (gross disturbances in chromosome alignment on the meiotic spindle of oocytes) results from the complex interplay of signals regulating folliculogenesis (thus increasing the risk of non-disjunction errors), it has been suggested that it may be possible to develop prophylactic treatments that can reduce the risk of age-related aneuploidy. DHEA may, indeed, be a first such drug.

Assuming such a more universal effect of DHEA supplementation on aneuploidy rates, supplementation should also be investigated for infertile women in general and, maybe, even for normally fertile women above age 35, who could receive DHEA as a routine preconception supplement, akin to prenatal vitamins. Should efficacy of DHEA supplementation in such a general population be proven, the potential significance of such a finding on public health could be considerable.

As stated herein, and supported at least by the examples herein, DHEA supplementation for at least two months increases egg numbers and egg quality and, therefore, also embryo numbers and quality. DHEA also improves spontaneous pregnancy rates, IVF pregnancy rates, cumulative pregnancy rates and time to conception in prognostically otherwise highly unfavorable patients. Further, DHEA statistically reduces miscarriage rates, probably, at least partially, by reducing aneuploidy rates. Moreover, DHEA probably also increases the male/female birth ratio. The effects of DHEA increase over time, reaching peaks after approximately four to five months of supplementation. It is suggested that the peak occurs at four to five months because this time period is similar to the time period of a complete follicular recruitment cycle.

While the foregoing written description of the invention enables one of ordinary skill to make and use what is considered presently to be the best mode thereof, those of ordinary skill will understand and appreciate the existence of variations, combinations, and equivalents of the specific exemplary embodiments thereof. The invention is therefore to be limited not by the exemplary embodiments herein, but by all embodiments within the scope and spirit of the appended claims.

What is claimed is:

1. A method of decreasing aneuploidy rates in human embryos comprising administering an androgen to a female for at least two months.

2. A method according to claim 1, wherein said female is human.

3. A method according to claim 1, wherein said androgen is dehydroepiandrosterone.

4. A method according to claim 3, wherein said dehydroepiandrosterone administration comprises between 50 and 100 mg per day of said dehydroepiandrosterone.

5. A method according to claim 3, wherein said dehydroepiandrosterone administration comprises between 15 mg and 40 mg of said dehydroepiandrosterone administered about three times a day.

6. A method of decreasing time to pregnancy and increasing pregnancy rates in females comprising administering an androgen for at least two months.

7. A method according to claim 1, wherein the administering step decreases miscarriage rates.

8. A method according to claim 1, wherein said female has been diagnosed with diminished ovarian reserve.

9. A method according to claim 1, further comprising administering microdose agonist flare to said female.

10. A method according to claim 1, further comprising administering maximal dosage of gonadotropins to said female.

11. A method according to claim 7, further comprising decreasing miscarriage rates by at least one-third.

* * * * *